(12) United States Patent
Lanza et al.

(10) Patent No.: US 7,255,875 B2
(45) Date of Patent: Aug. 14, 2007

(54) INTEGRIN TARGETED IMAGING AGENTS

(75) Inventors: Gregory M. Lanza, St. Louis, MO (US); Samuel A. Wickline, St. Louis, MO (US); Tom Harris, Salem, NH (US)

(73) Assignees: Barnes-Jewish Hospital, St. Louis, MO (US); Bristol Myers Squibb Medical Imaging, Inc., North Billerica, MA (US)

( * ) Notice: Subject to any disclaimer, the term of this patent is extended or adjusted under 35 U.S.C. 154(b) by 94 days.

(21) Appl. No.: 10/351,463

(22) Filed: Jan. 24, 2003

(65) Prior Publication Data

US 2004/0058951 A1     Mar. 25, 2004

Related U.S. Application Data

(60) Provisional application No. 60/351,390, filed on Jan. 24, 2002.

(51) Int. Cl.
    *A61K 9/66* (2006.01)
(52) U.S. Cl. ............. 424/455; 424/9.321; 424/9.32; 424/9.3
(58) Field of Classification Search ........... 424/9.3, 424/9.32, 9.321, 455, 489
    See application file for complete search history.

(56) References Cited

U.S. PATENT DOCUMENTS

| 5,520,904 A | 5/1996 | Nosco et al. |
| 5,571,498 A | 11/1996 | Cacheris et al. ......... 424/9.365 |
| 5,614,170 A | 3/1997 | Cacheris et al. ......... 424/9.365 |
| 5,690,907 A | 11/1997 | Lanza et al. ................ 424/9.5 |
| 5,780,010 A | 7/1998 | Lanza et al. ............... 424/9.32 |
| 5,958,371 A | 9/1999 | Lanza et al. ............... 424/1.21 |
| 5,989,520 A | 11/1999 | Lanza et al. ............... 424/9.32 |
| 6,130,231 A | 10/2000 | Wityak et al. .............. 514/312 |
| 6,153,628 A | 11/2000 | Jin et al. .................... 514/340 |
| 6,322,770 B1 | 11/2001 | Rajopadhye et al. ...... 424/1.65 |
| 2002/0127182 A1 | 9/2002 | Sherry et al. ............ 424/9.363 |

FOREIGN PATENT DOCUMENTS

| WO | WO 99/58162 | 11/1999 |
| WO | WO 00/35488 | 6/2000 |
| WO | WO 00/35492 | 6/2000 |
| WO | WO 00/35887 | 6/2000 |
| WO | WO 01/97848 | 12/2001 |
| WO | WO 02/060524 | 8/2002 |

OTHER PUBLICATIONS

Anderson et al., Magn. Reson. Med. (2000) 44:433-439.
Haubner et al., J. Nucl. Med. (1999) 40:1061-1071.
Haubner et al., J. Nucl. Med. (2001) 42:326-336.
Kerr et al., Anticancer Res. (1999) 19:959-968.
Sipkins et al., Nature Med. (1998) 4:623-626.
Storgard et al., J. Clin. Invest. (1999) 103:47-53.
Goodman et al., Journal of Medicinal Chemistry (2002) 45(5):1045-1051.
Supplementary Partial European Search Report for EP 03707550.4, mailed on Jul. 12, 2006, 5 pages.
Winter et al., Circulation (2002) 106(19):II-151 (Abstracts from Scientific Sessions).

*Primary Examiner*—Dameron L. Jones
(74) *Attorney, Agent, or Firm*—Morrison & Foerster LLP

(57) ABSTRACT

Emulsions preferably of nanoparticles formed from high boiling liquid perfluorochemical substances, said particles coated with a lipid/surfactant coating are made specific to regions of activated endothelial cells by coupling said nanoparticles to a ligand specific for $\alpha_v\beta_3$ integrin, other than an antibody. The nanoparticles may further include biologically active agents, radionuclides, or other imaging agents.

9 Claims, 6 Drawing Sheets

T$_2$-Weighted     T$_1$ Enhancement

A.

B.

INTEGRIN TARGETED IMAGING AGENTS

CROSS-REFERENCE TO RELATED APPLICATIONS

This application claims benefit under 35 U.S.C. § 119(e) to provisional application No. 60/351,390 filed Jan. 24, 2002. The contents of this application are incorporated herein by reference.

TECHNICAL FIELD

The invention relates to nanoparticle-based emulsions that are specifically targeted to integrins employing $\alpha_v\beta_3$-specific targeting agents. More specifically, the invention relates to the use of non-antibody based compositions for such targeting.

BACKGROUND ART

The value of nanoparticulate compositions composed of perfluorocarbon nanoparticles coated with a surfactant layer to facilitate binding of desired components for imaging of various types is well established. See, for example, U.S. Pat. Nos. 5,690,907; 5,780,010; 5,989,520; 5,958,371; and PCT publication WO 02/060524, the contents of which are incorporated herein by reference. These documents describe emulsions of perfluorocarbon nanoparticles that are coupled to various targeting agents and to desired components, such as MRI imaging agents, radionuclides, and/or bioactive agents. Other compositions that have been used for targeted imaging include those disclosed in PCT publications WO 99/58162; WO 00/35488; WO 00/35887; and WO 00/35492. The contents of these publications are also incorporated herein by reference.

The integrin $\alpha_v\beta_3$, which binds to vitronectin, is recognized as a marker for neovasculature. It is relatively selective for activated endothelial cells and essentially unexpressed on mature, quiescent cells. Based on this characteristic, it has been attempted to use antagonists to this integrin as anticancer agents. Kerr, J. S., et al., *Anticancer Res.* (1999) 19:959-968 describe peptide mimetics which were able to decrease neovasculature formation in a mouse model system. U.S. Pat. No. 6,153,628 describes 1,3,4-thiadiazoles and 1,3,4-oxadiazoles that are $\alpha_v\beta_3$ antagonists and are said to be useful in the treatment of disorders related to angiogenesis, including inflammation, bone degradation, tumors, metastases, thrombosis, and cell aggregation related conditions. U.S. Pat. Nos. 6,130,231 and 6,322,770 disclose fused heterocycles that are $\alpha_v\beta_3$ antagonists and useful for the same purposes, as does PCT publication WO 01/97848.

The WO 01/97848 publication discloses specific compounds that can be linked to ancillary substances, optionally through linker moieties, wherein these ancillary substances may include radionuclides, substances useful in magnetic resonance imaging, and X-ray contrast agents. This publication also discloses the use of these compounds coupled to certain ultrasound contrast agents, typically containing gaseous bubbles.

In addition to its expression in activated endothelial cells, $\alpha_v\beta_3$ is expressed on vascular smooth muscle cells, including macrophage in the walls of the vasculature. This complex binds cells to the surrounding matrix and is thus employed by cells in the course of migration. Accordingly, $\alpha_v\beta_3$ plays a role in restenosis by assisting the movement of cells into the lumen. A key component of restenosis involves vascular smooth muscle cell activation, proliferation and migration. Integrin heterodimers, in particular the $\alpha_v\beta_3$ integrin, are recognized as critical elements in these processes by providing cell adhesion to the extracellular matrix, inducing extracellular metalloproteinase expression, and facilitating smooth muscle cell migration. The $\alpha_v\beta_3$ integrin is widely distributed among endothelial cells, stimulated monocytes, T-lymphocytes, fibroblasts, vascular smooth muscle cells and platelets and binds to several extracellular matrix protein ligands including osteopontin, vitronectin, thrombospondin, and denatured collagens.

Antagonism of integrin mediated cell-matrix interactions within the balloon-stretched vessel walls inhibits inflammatory cell recruitment to the injury site, limits smooth muscle cell proliferation and migration, and diminishes extracellular matrix protein synthesis. Selective and nonselective blockade of integrins with cyclic RGD peptide antagonists have limited neointimal hyperplasia in several animal models of restenosis.

Restenosis is associated most often with angioplasty wherein, in an attempt to expand the vasculature using balloon catheters, the vasculature is broken, exposing the vascular smooth muscle cells. The resulting fractures require the movement of cells into the lumen; the $\alpha_v\beta_3$ acts to assist the migration through the matrix of collagen and fibrin to accomplish this. Accordingly, compositions that target $\alpha_v\beta_3$ may also be used to target smooth muscle cells and to image restenoses, in particular those associated with balloon angioplasty, and to deliver anti-proliferation agents such as paclitaxel, rapamycin, and other therapeutic moieties such as radionuclides, small molecules, peptides and nucleic acids.

While stent-based delivery systems offer the possibility of focal therapeutic drug effects within the tunica media of arteries without incurring the adverse side effects of systemic drug administration, and produce high local intimal concentrations of drug proximate to the stent-strut-arterial wall contact points, persistent high antiproliferative drug concentrations within the intima can impair arterial wall healing and reendothelialization, which promotes inflammation of the lumen lining and restenosis. The invention compositions avoid these problems.

It appears most peptidomimetics and neutralizing antibody $\alpha_v\beta_3$ antagonists have short half-lives and occupy the receptor for $\alpha_v\beta_3$ only transiently. The integrin-specific nanoparticles of the invention can target and block the binding of integrins exposed on smooth muscle cells by arterial overstretch injury as well as deliver a variety of therapeutic agents directly to cells that could inhibit inflammatory and restenosis processes and provide for molecular imaging for new, prognostic data relating the extent and severity of balloon injury to subsequent restenosis. The invention compositions avoid these problems.

Antibodies that are specific for $\alpha_v\beta_3$ integrin have been described in U.S. Pat. No. 6,171,588. These antibodies have been used in targeted magnetic resonance imaging (MRI) in a report by Sipkins, D. A., et al., *Nature Med.* (1998) 4:623-626; in this case coupled to the surface of liposomes via avidin linker proteins.

The use of antibodies directed to $\alpha_v\beta_3$ as a targeting agent for MRI using perfluorocarbon emulsions carrying chelated gadolinium has also been described by Anderson, S. A., et al., *Magn. Reson. Med.* (2000) 44:433-439, and in the above noted PCT publication WO 02/060524. Peptide ligands that are targeted to integrins have also been used as antagonists and have been suggested as a therapeutic strategy for rheumatoid arthritis by Storgard, C. M., et al., *J. Clin. Invest.* (1999) 103:47-53, who employed cyclic peptides containing the "RGD" type sequence known to interact with integrins.

Similar cyclic peptides were employed by Haubner, R., et al, *J. Nucl. Med.* (1999) 40:1061-1071 for tumor imaging by coupling the cyclic peptides directly to radionuclides. In an additional paper, the use of glycosylated forms of the cyclic peptides both for radiolabeling and PET is suggested by Haubner, R., et al., *J. Nucl. Med.* (2001) 42:326-336.

To applicants' knowledge, $\alpha_v\beta_3$-specific moieties other than antibodies have not been suggested for use as targeting agents in delivering image-aiding nanoparticulate emulsions or in delivering emulsions containing bioactive agents to regions containing activated endothelial cells such as sites of inflammation, tumors, atherosclerotic plaques, and restenoses.

DISCLOSURE OF THE INVENTION

The invention is directed to compositions and methods for imaging and drug delivery wherein non-antibody, $\alpha_v\beta_3$-specific moieties are used as targeting agents to deliver nanoparticle emulsions to regions containing high levels of angiogenesis, such as tumors, regions of inflammation, atherosclerotic regions, and restenoses. The use of these agents in the context of imaging nanoparticle emulsions results in improved image quality and the opportunity for targeted drug delivery.

Thus, in one aspect, the invention is directed to a method to deliver a nanoparticulate emulsion to a target tissue, wherein said target tissue is characterized by high levels of $\alpha_v\beta_3$ which method comprises administering to a subject comprising such tissue an emulsion of nanoparticles wherein said nanoparticles are coupled to a ligand specific for $\alpha_v\beta_3$, with the proviso that said ligand is other than an antibody or fragment thereof.

In other aspects, the invention is directed to compositions useful in the method of the invention, and to kits containing components of the compositions that can be assembled to perform the invention methods. The kits will typically provide emulsions that contain reactive groups that can bind to targeting agents provided separately, or that can bind to ancillary substances useful for imaging or drug delivery.

MODES OF CARRYING OUT THE INVENTION

Figure 1:
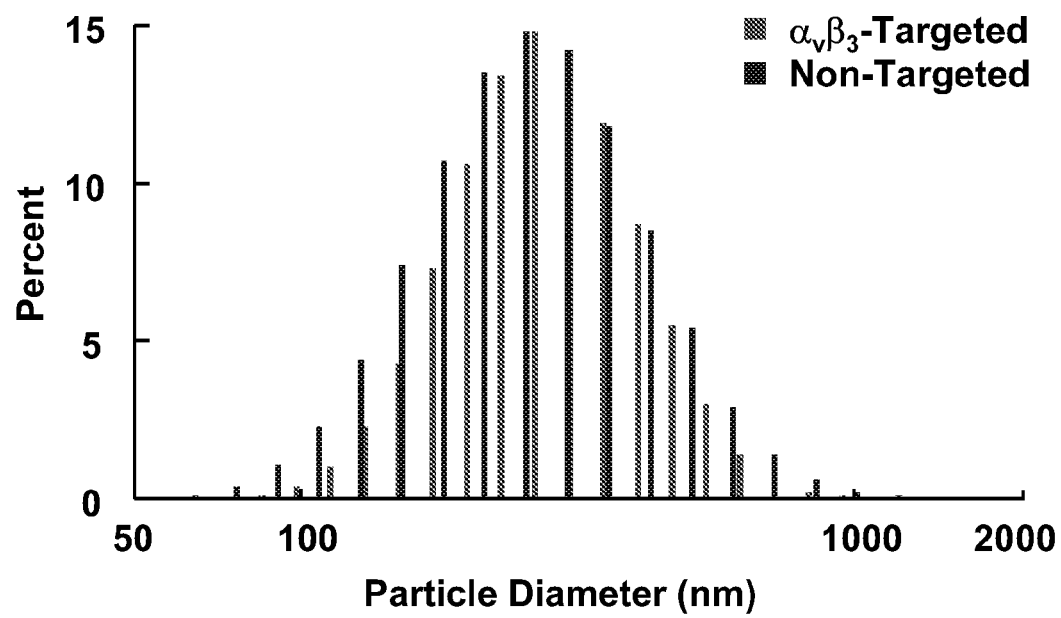
FIG. 1 shows the particle size distribution of $\alpha_v\beta_3$ targeted and non-targeted nanoparticles.

The present invention offers an approach whereby superior imaging of sites of activated endothelial cell concentrations can be obtained. Various emulsions which are useful in imaging can be employed. When used alone, the nanoparticle-containing emulsions are useful as contrast agents for ultrasound imaging. For use in magnetic resonance imaging or in X-ray imaging, it may be desirable to employ a transition metal as a contrast agent; if the nanoparticles comprise fluorocarbons, however, the fluorocarbon itself is useful in obtaining an image. Radionuclides are also useful both as diagnostic and therapeutic agents. In addition, reagents for optical imaging, such as fluorophores may also be associated with the nanoparticles. In addition, or alternatively, the nanoparticles in the emulsion may contain one or more bioactive agents.

Any nanoparticulate emulsion may be used. For example, PCT publication WO95/03829 describes oil emulsions where the drug is dispersed or solubilized inside an oil droplet and the oil droplet is targeted to a specific location by means of a ligand. U.S. Pat. No. 5,542,935 describes site-specific drug delivery using gas-filled perfluorocarbon microspheres. The drug delivery is accomplished by permitting the microspheres to home to the target and then effecting their rupture. Low boiling perfluoro compounds are used to form the particles so that the gas bubbles can form.

However, it is preferred to employ emulsions wherein the nanoparticles are based on high boiling perfluorocarbon liquids such as those described in U.S. Pat. No. 5,958,371 referenced above. The liquid emulsion contains nanoparticles comprised of relatively high boiling perfluorocarbons surrounded by a coating which is composed of a lipid and/or surfactant. The surrounding coating is able to couple directly to a targeting moiety or can entrap an intermediate component which is covalently coupled to the targeting moiety, optionally through a linker, or may contain a non-specific coupling agent such as biotin. Alternatively, the coating may be cationic so that negatively charged targeting agents such as nucleic acids, in general or aptamers, in particular, can be adsorbed to the surface.

In addition to the targeting $\alpha_v\beta_3$ ligand, the nanoparticles may contain associated with their surface an "ancillary agent" useful in imaging and/or therapy a radionuclide, a contrast agent for magnetic resonance imaging (MRI) or for X-ray imaging, a fluorophore and/or a biologically active compound. The nanoparticles themselves can serve as contrast agents for ultrasound imaging.

The preferred emulsion is a nanoparticulate system containing a high boiling perfluorocarbon as a core and an outer coating that is a lipid/surfactant mixture which provides a vehicle for binding a multiplicity of copies of one or more desired components to the nanoparticle. The construction of the basic particles and the formation of emulsions containing them, regardless of the components bound to the outer surface is described in the above-cited patents to the present applicants, U.S. Pat. No. 5,690,907 and 5,780,010; and patents issued on daughter applications U.S. Pat. Nos. 5,989,520 and 5,958,371 and incorporated herein by reference.

The high boiling fluorochemical liquid is such that the boiling point is higher than that of body temperature—i.e., 37° C. Thus, fluorochemical liquids which have boiling points at least 30° C. are preferred, more preferably 37° C., more preferably above 50° C., and most preferably above about 90° C. The "fluorochemical liquids" useful in the invention include straight and branched chain and cyclic perfluorocarbons including perfluorinated compounds which have other functional groups. "Perfluorinated compounds" includes compounds that are not pure perfluorocarbons but rather wherein other halo groups may be present. These include perfluorooctylbromide, and perfluorodichlorooctane, for example.

Perfluorinated compounds as thus defined are preferred.

Useful perfluorocarbon emulsions are disclosed in U.S. Pat. Nos. 4,927,623, 5,077,036, 5,114,703, 5,171,755, 5,304,325, 5,350,571, 5,393,524, and 5,403,575, which are incorporated herein by reference, and include those in which the perfluorocarbon compound is perfluorodecalin, perfluorooctane, perfluorodichlorooctane, perfluoro-n-octyl bromide, perfluoroheptane, perfluorodecane, perfluorocyclohexane, perfluoromorpholine, perfluorotripropylamine, perfluortributylamine, perfluorodimethylcyclohexane, perfluorotrimethylcyclohexane, perfluorodicyclohexyl ether, perfluoro-n-butyltetrahydrofuran, and compounds that are structurally similar to these compounds and are partially or fully halogenated (including at least some fluorine substituents) or partially or fully fluorinated including perfluoroalkylated ether, polyether or crown ether.

The lipid/surfactants used to form an outer coating on the nanoparticles (that will contain the coupled ligand or entrap reagents for binding desired components to the surface) include natural or synthetic phospholipids, fatty acids, cholesterols, lysolipids, sphingomyelins, and the like, including lipid conjugated polyethylene glycol. Various commercial anionic, cationic, and nonionic surfactants can also be employed, including Tweens, Spans, Tritons, and the like. Some surfactants are themselves fluorinated, such as perfluorinated alkanoic acids such as perfluorohexanoic and perfluorooctanoic acids, perfluorinated alkyl sulfonamide, alkylene quaternary ammonium salts and the like. In addition, perfluorinated alcohol phosphate esters can be employed. Cationic lipids included in the outer layer may be advantageous in entrapping ligands such as nucleic acids, in particular aptamers. Typical cationic lipids may include DOTMA, N-[1-(2,3-dioleoyloxy)propyl]-N,N,N-trimethylammonium chloride; DOTAP, 1,2-dioleoyloxy-3-(trimethylammonio)propane; DOTB, 1,2-dioleoyl-3-(4'-trimethylammonio)butanoyl-sn-glycerol,1,2-diacyl-3-trimethylammonium-propane; 1,2-diacyl-3-dimethylammonium-propane; 1,2-diacyl-sn-glycerol-3-ethyl phosphocholine; and 3β-[N',N'-dimethylaminoethane)-carbamol]cholesterol-HCl.

In preferred embodiments, included in the lipid/surfactant coating are components with reactive groups that can be used to couple the $\alpha_v\beta_3$ ligand and/or the ancillary substance useful for imaging or therapy. As will be described below, the lipid/surfactant components can be coupled to these reactive groups through functionalities contained in the lipid/surfactant component. For example, phosphatidylethanolamine may be coupled through its amino group directly to a desired moiety, or may be coupled to a linker such as a short peptide which may provide carboxyl, amino, or sulftydryl groups as described below. Alternatively, standard linking agents such a maleimides may be used. A variety of methods may be used to associate the targeting ligand and the ancillary substances to the nanoparticles; these strategies may include the use of spacer groups such as polyethyleneglycol or peptides, for example.

The lipid/surfactant coated nanoparticles are typically formed by microfluidizing a mixture of the fluorocarbon lipid which forms the core and the lipid/surfactant mixture which forms the outer layer in suspension in aqueous medium to form an emulsion. In this procedure, the lipid/surfactants may already be coupled to additional ligands when they are coated onto the nanoparticles, or may simply contain reactive groups for subsequent coupling. Alternatively, the components to be included in the lipid/surfactant layer may simply be solubilized in the layer by virtue of the solubility characteristics of the ancillary material. Sonication or other techniques may be required to obtain a suspension of the lipid/surfactant in the aqueous medium. Typically, at least one of the materials in the lipid/surfactant outer layer comprises a linker or functional group which is useful to bind the additional desired component or the component may already be coupled to the material at the time the emulsion is prepared.

For coupling by covalently binding the targeting ligand or other organic moiety (such as a chelating agent for a paramagnetic metal) to the components of the outer layer, various types of bonds and linking agents may be employed. Typical methods for forming such coupling include formation of amides with the use of carbodiamides, or formation of sulfide linkages through the use of unsaturated components such as maleimide. Other coupling agents include, for example, glutaraldehyde, propanedial or butanedial, 2-iminothiolane hydrochloride, bifunctional N-hydroxysuccinimide esters such as disuccinimidyl suberate, disuccinimidyl tartrate, bis[2-(succinimidooxycarbonyloxy)ethyl]sulfone, heterobifunctional reagents such as N-(5-azido-2-nitrobenzoyloxy)succinimide, succinimidyl 4-(N-maleimidomethyl) cyclohexane-1-carboxylate, and succinimidyl 4-(p-maleimidophenyl)butyrate, homobifunctional reagents such as 1,5-difluoro-2,4-dinitrobenzene, 4,4'-difluoro-3,3'-dinitrodiphenylsulfone, 4,4'-diisothiocyano-2,2'-disulfonic acid stilbene, p-phenylenediisothiocyanate, carbonylbis(L-methionine p-nitrophenyl ester), 4,4'-dithiobisphenylazide, erythritolbiscarbonate and bifunctional imidoesters such as dimethyl adipimidate hydrochloride, dimethyl suberimidate, dimethyl 3,3'-dithiobispropionimidate hydrochloride and the like. Linkage can also be accomplished by acylation, sulfonation, reductive amination, and the like. A multiplicity of ways to couple, covalently, a desired ligand to one or more components of the outer layer is well known in the art. The ligand itself may be included in the surfactant layer if its properties are suitable. For example, if the ligand contains a highly lipophilic portion, it may itself be embedded in the lipid/surfactant coating. Further, if the ligand is capable of direct adsorption to the coating, this too will effect its coupling. For example, nucleic acids, because of their negative charge, adsorb directly to cationic surfactants.

The ligand may bind directly to the nanoparticle, i.e., the ligand is associated with the nanoparticle itself. Alternatively, indirect binding such as that effected through biotin/avidin may be employed typically for the $\alpha_v\beta_3$-specific ligand. For example, in biotin/avidin mediated targeting, the $\alpha_v\beta_3$ ligand is coupled not to the emulsion, but rather coupled, in biotinylated form to the targeted tissue.

Ancillary agents that may be coupled to the nanoparticles through entrapment in the coating layer include radionuclides. Radionuclides may be either therapeutic or diagnostic; diagnostic imaging using such nuclides is well known and by targeting radionuclides to undesired tissue a therapeutic benefit may be realized as well. Typical diagnostic radionuclides include $^{99m}$Tc, $^{95}$Tc, $^{111}$In, $^{62}$Cu, $^{64}$Cu, $^{67}$Ga, and $^{68}$Ga, and therapeutic nuclides include $^{186}$Re, $^{188}$Re, $^{153}$Sm, $^{166}$Ho, $^{177}$Lu, $^{149}$Pm, $^{90}$Y, $^{212}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, and $^{192}$Ir. The nuclide can be provided to a preformed emulsion in a variety of ways. For example, $^{99}$Tc-pertechnate may be mixed with an excess of stannous chloride and incorporated into the preformed emulsion of nanoparticles. Stannous oxinate can be substituted for stannous chloride. In addition, commercially available kits, such as the HM-PAO (exametazine) kit marketed as Ceretek® by Nycomed Amersham can be used. Means to attach various radioligands to the nanoparticles of the invention are understood in the art.

Chelating agents containing paramagnetic metals for use in magnetic resonance imaging can also be employed as ancillary agents. Typically, a chelating agent containing a paramagnetic metal is associated with the lipids/surfactants of the coating on the nanoparticles and incorporated into the initial mixture which is sonicated. The chelating agent can be coupled directly to one or more of components of the coating layer. Suitable chelating agents include a variety of multi-dentate compounds including EDTA, DPTA, DOTA, and the like. These chelating agents can be coupled directly to functional groups contained in, for example, phosphatidyl ethanolamine, bis-oleate, and the like, or through linking groups.

The paramagnetic metals useful in the MRI contrast agents of the invention include rare earth metals, typically, manganese, ytterbium, gadolinium, europium, and the like. Iron ions may also be used.

Other ancillary agents include fluorophores such as fluorescein, dansyl, quantum dots, and the like.

Included in the surface of the nanoparticle, in some embodiments of the invention, are biologically active agents. These biologically active agents can be of a wide variety, including proteins, nucleic acids, pharmaceuticals, and the like. Thus, included among suitable pharmaceuticals are antineoplastic agents, hormones, analgesics, anesthetics, neuromuscular blockers, antimicrobials or antiparasitic agents, antiviral agents, interferons, antidiabetics, antihistamines, antitussives, anticoagulants, and the like.

In all of the foregoing cases, whether the associated moiety is a targeting ligand for $\alpha_v\beta_3$ or is an ancillary agent, the defined moiety may be non-covalently associated with the lipid/surfactant layer, may be directly coupled to the components of the lipid/surfactant layer, or may be coupled to said components through spacer moieties.

Targeting Ligands

The emulsions of the present invention employ targeting agents that are ligands specific for the $\alpha_v\beta_3$ integrin other than an antibody or fragment thereof. In one embodiment, the ligand is a non-peptide organic molecule, such as those described in U.S. Pat. Nos. 6,130,231; 6,153,628; 6,322,770; and PCT publication WO 01/97848 referenced above, and incorporated herein by reference. "Non-peptide" moieties in general are those other than compounds which are simply polymers of amino acids, either gene encoded or non-gene encoded. Thus, "non-peptide ligands" are moieties which are commonly referred to as "small molecules" lacking in polymeric character and characterized by the requirement for a core structure other than a polymer of amino acids. The non-peptide ligands useful in the invention may be coupled to peptides or may include peptides coupled to portions of the ligand which are responsible for affinity to the $\alpha_v\beta_3$ moiety, but it is the non-peptide regions of this ligand which account for its binding ability.

One group of $\alpha_v\beta_3$-specific ligands that is particularly useful in the methods and compositions of the invention are of the formula (I):

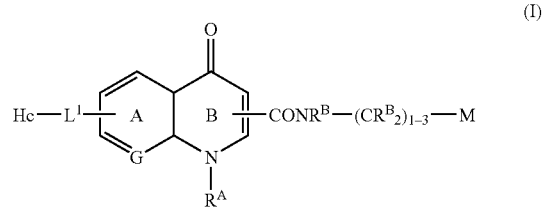

including stereoisomeric forms thereof, or mixtures of stereoisomeric forms thereof, or pharmaceutically acceptable salt or prodrug forms thereof, wherein:

Hc comprises guanidyl or comprises a heterocyclic ring containing N;

$L^1$ is a linker;

G is N or $CR^B$;

$R^A$ is a non-interfering substituent other than H;

each $R^B$ is independently H or a non-interfering substituent; and

M comprises an optionally substituted carboxylic, sulfonylic, or phosphoric acid group or an ester or amide thereof or is a 4- or 5-membered ring;

wherein each of ring A and ring B may optionally further be substituted with non-interfering substituents.

When appropriate, the compounds may be in the form of salts.

When the compounds of Formula (I) contain one or more chiral centers, the invention includes optically pure forms as well as mixtures of stereoisomers or enantiomers.

In the compounds of formula (I), the carboxylic, sulfonylic or phosphoric acid groups or esters or amides thereof included in M may be positioned in either orientation with respect to the molecule—i.e., a sulfonamide may be $SO_2N$— or —$NSO_2$—; in addition, multiple carboxylic, sulfonylic or phosphoric acid groups, esters or amides thereof may be included in tandem. These residues may further be substituted, and may be coupled to the components of the nanoparticles through various linking groups, including those which contain PEG and those that contain peptide linkages.

Preferred embodiments of M are selected from the group consisting of —$COR^B$, —$SO_3H$, —$PO_3H$, —$CONHNHSO_2CF_3$, —$CONHSO_2R^B$, —$CONHSO_2NHR^B$, —$NHCOCF_3$, —$NHCONHSO_2R^B$, —$NHSO_2R^B$, —$OPO_3H_2$, —$OSO_3H$, —$PO_3H_2$, —$SO_2NHCOR^B$, —$SO_2NHCO_2R^B$,

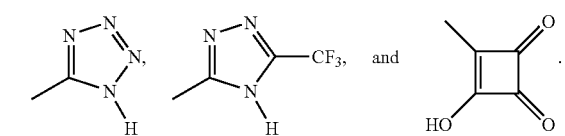

A "non-interfering substituent" is a substituent which does not destroy the ability of the compounds of formula (I) to bind to $\alpha_v\beta_3$. The substituent may alter the strength of binding, but the binding must still be detectable using standard methods, such as detection of label bound to a solid support wherein the solid support is coupled to $\alpha_v\beta_3$. The essential features of the compounds of formula (I) are set forth in the formula, and clearly a variety of substituents may further be included without even substantially altering the ability of the compound thus to bind. The skilled artisan can readily assess, for any particular embodiment of $R^B$ whether the binding characteristics to $\alpha_v\beta_3$ are sufficiently satisfactory to warrant the incorporation of the $R^B$ embodiment tested. Thus, for any arbitrarily chosen embodiment, it is a straightforward matter to determine whether the substituent interferes or does not interfere.

Thus, the essential features of the molecule are tightly defined. The positions which are occupied by "noninterfering substituents" can be substituted by conventional inorganic or organic moieties as is understood in the art. It is irrelevant to the present invention to test the outer limits of such substitutions. The essential features of the compounds are those set forth with particularity herein.

In addition, $L^1$ is described herein as a linker. The nature of such a linker is less important that the distance it imparts between the portions of the molecule. Typical linkers include alkylene, i.e. $(CH_2)_n$; alkenylene—i.e., an alkylene moiety which contains a double bond, including a double bond at one terminus. Other suitable linkers include, for example, substituted alkylenes or alkenylenes, carbonyl moieties, and the like.

"Hydrocarbyl residue" refers to a residue which contains only carbon and hydrogen. The residue may be aliphatic or aromatic, straight-chain, cyclic, branched, saturated or unsaturated. The hydrocarbyl residue, when so stated however, may contain heteroatoms over and above, or substituted for, the carbon and hydrogen members of the substituent residue. Thus, when specifically noted as containing such heteroatoms, the hydrocarbyl residue may also contain carbonyl groups, amino groups, hydroxyl groups and the like, or contain heteroatoms within the "backbone" of the hydrocarbyl residue.

"Alkyl," "alkenyl" and "alkynyl" include straight- and branched-chain and cyclic monovalent substituents. Examples include methyl, ethyl, isobutyl, cyclohexyl, cyclopentylethyl, 2-propenyl, 3-butynyl, and the like. Typically, the alkyl, alkenyl and alkynyl substituents contain 1-10C (alkyl) or 2-10C (alkenyl or alkynyl). Preferably they contain 1-6C (alkyl) or 2-6C (alkenyl or alkynyl). Such moieties containing heteroatoms are similarly defined but may contain 1-2 O, S, $P_1$Si or N heteroatoms or combinations thereof within the backbone residue.

"Acyl" encompasses the definitions of alkyl, alkenyl, alkynyl and the related hetero-forms which are coupled to an additional residue through a carbonyl group.

"Aromatic" or "aryl" moiety refers to a monocyclic or fused bicyclic moiety such as phenyl or naphthyl; "heteroaromatic" also refers to monocyclic or fused bicyclic ring systems containing one or more heteroatoms selected from O, S and N. The inclusion of a heteroatom permits inclusion of 5-membered rings as well as 6-membered rings. Thus, typical aromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl and the like. Any monocyclic or fused ring bicyclic system which has the characteristics of aromaticity in terms of electron distribution throughout the ring system is included in this definition. Typically, the ring systems contain 5-12 ring member atoms.

The "non-interfering substituents" are typically halo, OH, SH, $NH_2$, $NO_2$, or other inorganic substituents or are hydrocarbyl residues (1-20C) containing 0-6 heteroatoms selected from O, S, P, Si, and N. Preferably the heteroatoms are O, S and/or N. For example, the hydrocarbyl residue may be alkyl, alkenyl, alkynyl, aryl, arylalkyl, which substituents may contain the above mentioned heteroatoms and/or may themselves be substituted with 1-6 substituents. The substituents on aryl moieties or on suitable heteroatoms include alkyl, alkenyl, alkynyl, additional aryl, or arylalkyl, arylalkenyl, and arylalkynyl. Substituents which may occur on non-cyclic carbon chains, including appropriate heteroatoms, include substituted forms of these moieties and/or heteroatom-containing forms thereof as well as halo, OR, $NR_2$, SR, SOR, $SO_2R$, OCOR, NRCOR, $NRCONR_2$, NRCOOR, $OCONR_2$, RCO, COOR, $SO_3R$, $CONR_2$, $SO_2NR_2$, $NRSO_2NR_2$, CN, $CF_3$, $R_3Si$, and $NO_2$ where each R is independently alkyl, alkenyl, aryl, etc., or heteroforms thereof. Two substituents may form a ring or =O.

Two $R^B$ on adjacent positions or on the same C or N can be joined to form a fused, optionally substituted aromatic or nonaromatic saturated or unsaturated ring which contains 3-8 members or two $R^B$ may be =O or an oxime, oxime ether, oxime ester or ketal thereof.

In one set of embodiments, in the compounds of formula (I), Hc is an optionally substituted 5 or 6 membered ring containing one or two nitrogens. Preferred substituents include amines.

One set of embodiments of $L^1$ includes alkylene chains of 1-4 member atoms of which one or two non-adjacent members may be heteroatoms which are N, S or O, preferably N. Preferred embodiments for G include N and CH.

Preferred embodiments of $R^B$ include H, alkyl (1-1C), alkenyl (2-1C), acyl (1-1C), arylalkyl or arylacyl wherein alkyl and acyl are defined as above and aryl contains 5-12 ring members including, optionally, heteroatoms selected from N, O and S. When $R^B$ is substituted onto a carbon, $R^B$ may be COOR (where R is H or alkyl (1-1C), or $CONR_2$ wherein R is as previously defined, OOCR or NROCR where R is as previously defined, halo, $CF_3$, and the like.

One group of $\alpha_v\beta_3$-specific ligands that are embodiments of formula (I) useful in the invention are compounds of the formula (II):

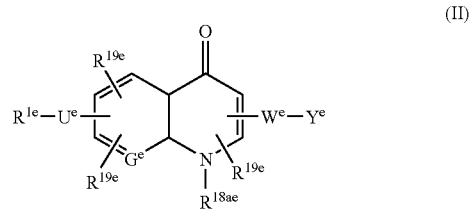

(II)

including stereoisomeric forms thereof, or mixtures of stereoisomeric forms thereof, or pharmaceutically acceptable salt or prodrug forms thereof, wherein $R^{1e}$ is selected from:

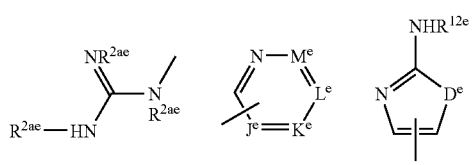

-continued

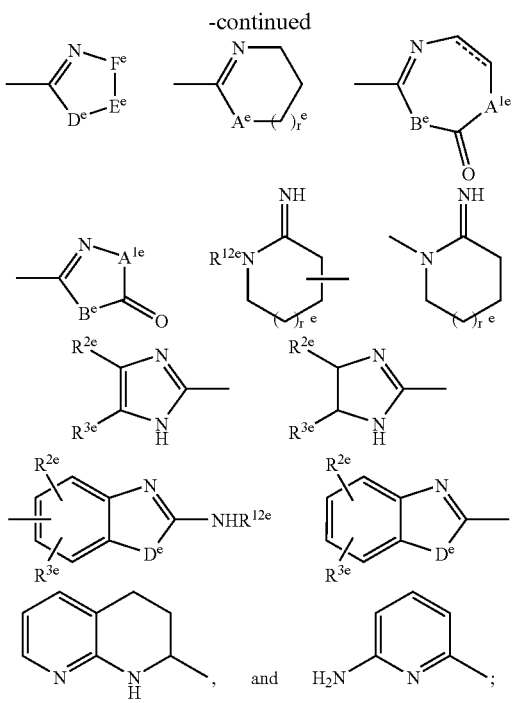

$A^e$ is —CH$_2$— or —N(R$^{10e}$)—;

$A^{1e}$ and $B^e$ are independently —CH$_2$— or —N(R$^{10e}$)—;

$D^e$ is —N(R$^{10e}$)— or —S—;

$E^e$-$F^e$ is —C(R$^{2e}$)=C(R$^{3e}$)— or —C(R$^{2e}$)$_2$C(R$^{3e}$)$_2$—;

$J^e$ is —C(R$^{2e}$)— or —N—;

$K_e$, $L^e$ and $M^e$ are independently —C(R$^{2e}$)— or —C(R$^{3e}$)—;

R$^{2e}$ and R$^{3e}$ are independently selected from:

H, C$_1$-C$_4$ alkoxy, NR$^{11e}$R$^{12e}$, halogen, NO$_2$, CN, CF$_3$, C$_1$-C$_6$ alkyl, C$_3$-C$_6$ alkenyl, C$_3$-C$_7$ cycloalkyl, C$_3$-C$_7$ cycloalkyl(C$_1$-C$_4$ alkyl), aryl(C$_1$-C$_6$ alkyl)-, (C$_1$-C$_6$ alkyl)carbonyl, (C$_1$-C$_6$ alkoxy)carbonyl, arylcarbonyl, and aryl substituted with 0-4 R$^{7e}$, alternatively, when R$^{2e}$ and R$^{3e}$ are substituents on adjacent atoms, they can be taken together with the carbon atoms to which they are attached to form a 5-7 membered carbocyclic or 5-7 membered heterocyclic aromatic or nonaromatic ring system, said carbocyclic or heterocyclic ring being substituted with 0-2 groups selected from C$_1$-C$_4$ alkyl, C$_1$-C$_4$ alkoxy, halo, cyano, amino, CF$_3$ and NO$_2$;

R$^{2ae}$ is selected from:

H, C$_1$-C$_{10}$ alkyl, C$_2$-C$_6$ alkenyl, C$_3$-C$_{11}$ cycloalkyl, C$_3$-C$_7$ cycloalkyl(C$_1$-C$_4$ alkyl), aryl aryl(C$_1$-C$_4$ alkyl)-, (C$_2$-C$_7$ alkyl)carbonyl, arylcarbonyl, (C$_2$-C$_{10}$ alkoxy)carbonyl, C$_3$-C$_7$ cycloalkoxycarbonyl, C$_7$-C$_{11}$ bicycloalkoxycarbonyl, aryloxycarbonyl, aryl(C$_1$-C$_{10}$ alkoxy)carbonyl, C$_1$-C$_6$ alkylcarbonyloxy(C$_1$-C$_4$ alkoxy)carbonyl, arylcarbonyloxy(C$_1$-C$_4$ alkoxy)carbonyl, and C$_3$-C$_7$ cycloalkylcarbonyloxy(C$_1$-C$_4$ alkoxy)carbonyl;

R$^{7e}$ is selected from:

H, hydroxy, C$_1$-C$_4$ alkyl, C$_1$-C$_4$ alkoxy, aryl, aryl(C$_1$-C$_4$ alkyl)-, (C$_1$-C$_4$ alkyl)carbonyl, CO$_2$R$^{18ae}$, SO$_2$R$^{11e}$, SO$_2$NR$^{10e}$R$^{11e}$, OR$^{10e}$, and N(R$_{11e}$)R$^{12e}$;

wherein U$^e$ is selected from:

—(CH$_2$)$_n^e$—, —(CH$_2$)$_n^e$O(CH$_2$)$_m^e$—, —(CH$_2$)neN(R$^{12}$)(CH$_2$)$_m^e$—, —NH(CH$_2$)$_n^e$—, —(CH$_2$)$_n^e$C(=O)(CH$_2$)$_m^e$—, —(CH$_2$)$_n^e$S(O)$_p^e$(CH$_2$)$_m^e$—, —(CH$_2$)$_n^e$NHNH(CH$_2$)$_m^e$—, —N(R$^{10e}$)C(=O)—, —NHC(=O)(CH$_2$)$_n^e$—, —C(=O)N(R$^{10e}$)—, and —N(R$^{10e}$)S(O)$_p^e$—;

wherein G$^e$ is N or CR$^{19e}$;

wherein W$^e$ is —C(=O)—N(R$^{10e}$)—(C$_1$-C$_3$ alkylene)-, in which the alkylene group is substituted by R$^{8e}$ and by R$^{9e}$;

R$^{8e}$ and R$^{9e}$ are independently selected from:

H, CO$_2$R$^{18be}$, C(=O)R$^{18be}$, CONR$^{17e}$R$^{18be}$, C$_1$-C$_{10}$ alkyl substituted with 0-1 R$^{6e}$, C$_2$-C$_{10}$ alkenyl substituted with 0-1 R$^{6e}$, C$_2$-C$_{10}$ alkynyl substituted with 0-1 R$^{6e}$, C$_3$-C$_8$ cycloalkyl substituted with 0-1 R$^{6e}$, C$_5$-C$_6$ cycloalkenyl substituted with 0-1 R$^{6e}$, (C$_1$-C$_{10}$ alkyl)carbonyl, C$_3$-C$_{10}$ cycloalkyl(C$_1$-C$_4$ alkyl)-, phenyl substituted with 0-3 R$^{6e}$, naphthyl substituted with 0-3 R$^{6e}$, a 5-10 membered heterocyclic ring containing 1-3 N, O, or S heteroatoms, wherein said heterocyclic ring may be saturated, partially saturated, or fully unsaturated, said heterocyclic ring being substituted with 0-2 R$^{7e}$, C$_1$-C$_{10}$ alkoxy substituted with 0-2 R$^{7e}$, hydroxy, nitro, —N(R$^{10e}$)R$^{11e}$, —N(R$^{16e}$)R$^{17e}$, aryl(C$_0$-C$_6$ alkyl)carbonyl, aryl(C$_3$-C$_6$ alkyl), heteroaryl(C$_1$-C$_6$ alkyl), CONR$^{18ae}$R$^{20e}$, SO$_2$R$^{18ae}$, and SO$_2$NR$^{18ae}$R$^{20e}$, providing that any of the above alkyl, cycloalkyl, aryl or heteroaryl groups may be unsubstituted or substituted independently with 1-2 R$^{7e}$;

R$^{6e}$ is selected from:

H, C$_1$-C$_{10}$ alkyl, hydroxy, C$_1$-C$_{10}$ alkoxy, nitro, C$_1$-C$_{10}$ alkylcarbonyl, —N(R$^{11e}$)R$^{12e}$, cyano, halo, CF$_3$, CHO, CO$_2$R$^{18be}$, C(=O)R$^{18be}$, CONR$^{17e}$R$^{18be}$, OC(=O)R$^{10e}$, OR$^{10e}$, OC(=O)NR$^{10e}$R$^{11e}$, NR$^{10e}$C(=O)R$^{10e}$, NR$^{10e}$C(=O)OR$^{21e}$, NR$^{10e}$C(=O)NR$^{10e}$R$^{11e}$, NR$^{10e}$SO$_2$NR$^{10e}$R$^{11e}$, NR$^{10e}$SO$_2$R$^{21e}$, S(O)$_p$R$^{11e}$, SO$_2$NR$^{10e}$R$^{11e}$, aryl substituted with 0-3 groups selected from halogen, C$_1$-C$_6$ alkoxy, C$_1$-C$_6$ alkyl, CF$_3$, S(O)$_m^e$Me, and —NMe$_2$, aryl(C$_1$-C$_4$ alkyl)-, said aryl being substituted with 0-3 groups selected from halogen, C$_1$-C$_6$ alkoxy, C$_1$-C$_6$ alkyl, CF$_3$, S(O)$_p^e$Me, and —NMe$_2$, and a 5-10 membered heterocyclic ring containing 1-3 N, O, or S heteroatoms, wherein said heterocyclic ring may be saturated, partially saturated, or fully unsaturated, said heterocyclic ring being substituted with 0-2 R$^{7e}$;

R$^{10e}$ is selected from:

H, CF$_3$, C$_3$-C$_6$ alkenyl, C$_3$-C$_{11}$ cycloalkyl, aryl, (C$_3$-C$_{11}$ cycloalkyl)methyl, aryl(C$_1$-C$_4$ alkyl), and C$_1$-C$_{10}$ alkyl substituted with 0-2 R$^{6e}$;

R$^{11e}$ is selected from:

H, hydroxy, C$_1$-C$_8$ alkyl, C$_3$-C$_6$ alkenyl, C$_3$-C$_{11}$ cycloalkyl, (C$_3$-C$_{11}$ cycloalkyl) methyl, C$_1$-C$_6$ alkoxy, benzyloxy, aryl, heteroaryl, heteroaryl(C$_1$-C$_4$ alkyl)-, aryl(C$_1$-C$_4$ alkyl), adamantylmethyl, and C$_1$-C$_{10}$ alkyl substituted with 0-2 R$^{4e}$;

R$^{4e}$ is selected from:

H, C$_1$-C$_6$ alkyl, C$_3$-C$_7$ cycloalkyl, C$_3$-C$_7$ cycloalkyl(C$_1$-C$_4$ alkyl)-, (C$_1$-C$_{10}$ alkyl)carbonyl, aryl, heteroaryl, aryl (C$_1$-C$_6$ alkyl)-, and heteroaryl(C$_1$-C$_6$ alkyl)-, wherein said aryl or heteroaryl groups are substituted with 0-2 substituents independently selected from the group consisting of C$_1$-C$_4$ alkyl, C$_1$-C$_4$ alkoxy, F, Cl, Br, CF$_3$, and NO$_2$, alternatively, when $R^{10e}$ and $R^{11e}$ are both substituents on the same nitrogen atom (as in —$NR^{10e}R^{11e}$) they may be taken together with the nitrogen atom to which they are attached to form a heterocycle selected from: 3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, and 1-piperazinyl;

said heterocycle being substituted with 0-3 groups selected from: $C_1$-$C_6$ alkyl, aryl, heteroaryl, aryl($C_1$-$C_4$ alkyl)-, ($C_1$-$C_6$ alkyl)carbonyl, ($C_3$-$C_7$ cycloalkyl)carbonyl, ($C_1$-$C_6$ alkoxy)carbonyl, aryl($C_1$-$C_4$ alkoxy)carbonyl, $C_1$-$C_6$ alkylsulfonyl, and arylsulfonyl;

$R^{12e}$ is selected from:

H, $C_1$-$C_6$ alkyl, triphenylmethyl, methoxymethyl, methoxyphenyldiphenylmethyl, trimethylsilylethoxymethyl, ($C_1$-$C_6$ alkyl)carbonyl, ($C_1$-$C_6$ alkoxy)carbonyl, ($C_1$-$C_6$ alkyl)aminocarbonyl, $C_3$-$C_6$ alkenyl, $C_3$-$C_7$ cycloalkyl, $C_3$-$C_7$ cycloalkyl($C_1$-$C_4$ alkyl)-, aryl, heteroaryl($C_1$-$C_6$ alkyl)carbonyl, heteroarylcarbonyl, aryl ($C_1$-$C_6$ alkyl)-, ($C_1$-$C_6$ alkyl)carbonyl, arylcarbonyl, $C_1$-$C_6$ alkylsulfonyl, arylsulfonyl, aryl($C_1$-$C_6$ alkyl)sulfonyl, heteroarylsulfonyl, heteroaryl($C_1$-$C_6$ alkyl)sulfonyl, aryloxycarbonyl, and aryl($C_1$-$C_6$ alkoxy)carbonyl, wherein said aryl groups are substituted with 0-2 substituents selected from the group consisting of $C_1$-$C_4$ alkyl, $C_1$-$C_4$ alkoxy, halo, $CF_3$, and nitro;

$R^{16e}$ is selected from:

—C(=O)O$R^{18ae}$, —C(=O)$R^{18be}$, —C(=O)N($R^{18be}$)$_2$, —C(=O)NHSO$_2R^{18ae}$, —C(=O)NHC(=O)$R^{18be}$, —C(=O)NHC(=O)O$R^{18ae}$, —C(=O)NHSO$_2$NH$R^{18be}$, —SO$_2R^{18ae}$, —SO$_2$N($R^{18be}$)$_2$, and —SO$_2$NHC(=O)O$R^{18be}$;

$R^{17e}$ is selected from:

H, $C_1$-$C_6$ alkyl, $C_3$-$C_7$ cycloalkyl, $C_3$-$C_7$ cycloalkyl($C_1$-$C_4$ alkyl)-, aryl, aryl ($C_1$-$C_6$ alkyl)-, and heteroaryl($C_1$-$C_6^{alkyl}$);

wherein $R^{18ae}$ is selected from:

$C_1$-$C_8$ alkyl optionally substituted with a bond to $L_n$, $C_3$-$C_{11}$ cycloalkyl optionally substituted with a bond to $L_n$, aryl($C_1$-$C_6$ alkyl)-optionally substituted with a bond to $L_n$, heteroaryl($C_1$-$C_6$ alkyl)-optionally substituted with a bond to $L_n$, ($C_1$-$C_6$ alkyl)heteroaryl optionally substituted with a bond to $L_n$, biaryl($C_1$-$C_6$ alkyl) optionally substituted with a bond to $L_n$, heteroaryl optionally substituted with a bond to $L_n$, phenyl substituted with 3-4 $R^{19e}$ and optionally substituted with a bond to $L_n$, naphthyl substituted with 0-4 $R^{19e}$ and optionally substituted with a bond to $L_n$, and a bond to $L_n$, wherein said aryl or heteroaryl groups are optionally substituted with 0-4 $R^{19e}$;

$R^{18be}$ is H or $R^{18ae}$;

wherein $R^{19e}$ is selected from:

H, halogen, $CF_3$, $CO_2$H, CN, $NO_2$, —$NR^{11e}R^{12e}$, $OCF_3$, $C_1$-$C_8$ alkyl, $C_2$-$C_6$ alkenyl, $C_2$-$C_6$ alkynyl, $C_3$-$C_{11}$ cycloalkyl, $C_3$-$C_7$ cycloalkyl($C_1$-$C_4$ alkyl)-, aryl($C_1$-$C_6$ alkyl)-, $C_1$-$C_6$ alkoxy, $C_1$-$C_4$ alkoxycarbonyl, aryl, aryl-O—, aryl-SO$_2$—, heteroaryl, and heteroaryl-SO$_2$—, wherein said aryl and heteroaryl groups are substituted with 0-4 groups selected from hydrogen, halogen, $CF_3$, $C_1$-$C_3$ alkyl, and $C_1$-$C_3$ alkoxy;

$R^{20e}$ is selected from:

hydroxy, $C_1$-$C_{10}$ alkyloxy, $C_3$-$C_{11}$ cycloalkyloxy, aryloxy, aryl($C_1$-$C_4$ alkyl)oxy, $C_2$-$C_{10}$ alkylcarbonyloxy($C_1$-$C_2$ alkyl)oxy-, $C_2$-$C_{10}$ alkoxycarbonyloxy($C_1$-$C_2$ alkyl) oxy-, $C_2$-$C_{10}$ alkoxycarbonyl($C_1$-$C_2$ alkyl)oxy-, $C_3$-$C_{10}$ cycloalkylcarbonyloxy($C_1$-$C_2$ alkyl)oxy-, $C_3$-$C_{10}$ cycloalkoxycarbonyloxy($C_1$-$C_2$ alkyl)oxy-, $C_3$-$C_{10}$ cycloalkoxycarbonyl($C_1$-$C_2$ alkyl)oxy-, aryloxycarbonyl($C_1$-$C_2$ alkyl)oxy-, aryloxycarbonyloxy($C_1$-$C_2$ alkyl)oxy-, arylcarbonyloxy($C_1$-$C_2$ alkyl)oxy-, $C_1$-$C_5$ alkoxy($C_1$-$C_5$ alkyl)carbonyloxy($C_1$-$C_2$ alkyl)oxy, (5-($C_1$-$C_5$ alkyl)-1,3-dioxa-cyclopenten-2-one-yl)methyloxy, (5-aryl-1,3-dioxa-cyclopenten-2-one-yl)methyloxy, and ($R^{10e}$)($R^{11e}$)N—($C_1$-$C_{10}$alkoxy)-;

$R^{21e}$ is selected from:

$C_1$-$C_8$ alkyl, $C_2$-$C_6$ alkenyl, $C_3$-$C_{11}$ cycloalkyl, ($C_3$-$C_{11}$ cycloalkyl)methyl, aryl, aryl($C_1$-$C_4$ alkyl)-, and $C_1$-$C_{10}$ alkyl substituted with 0-2 $R^{7e}$;

$R^{22e}$ is selected from:

—C(=O)—$R^{18be}$, —C(=O)N($R^{18be}$)$_2$, —C(=O)NHSO$_2R^{18ae}$, —C(=O)NHC(=O)$R^{18be}$, —C(=O)NHC(=O)O$R^{18ae}$, and —C(=O)NHSO$_2$NH$R^{18be}$;

wherein $Y^e$ is selected from:

—CO$R^{20e}$, —SO$_3$H, —PO$_3$H, —CONHNHSO$_2CF_3$, —CONHSO$_2R^{18ae}$, —CONHSO$_2$NHR$^{18be}$, —NHCOCF$_3$, —NHCONHSO$_2R^{18ae}$, —NHSO$_2R^{18ae}$, —OPO$_3H_2$, —OSO$_3$H, —PO$_3H_2$, —SO$_2$NHCO$R^{18ae}$, —SO$_2$NHCO$_2R^{18ae}$,

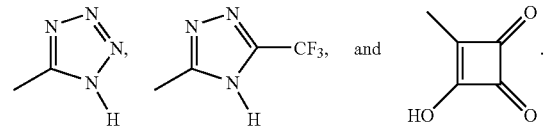

The ligand set forth above may be coupled through a linker to the materials contained in the lipid/surfactant coating of the particles. In one embodiment, the linkers are of the formula:

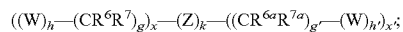

W is independently selected at each occurrence from the group: O, S, NH, NHC(=O), C(=O)NH, $NR^8$C(=O), C(=O)N $R^8$, C(=O), C(=O)O, OC(=O), NHC(=S) NH, NHC(=O)NH, SO$_2$, SO$_2$NH, (OCH$_2$CH$_2$)$_{20-200}$, (CH$_2$CH$_2$O)$_{20-200}$, (OCH$_2$CH$_2$CH$_2$)$_{20-200}$, (CH$_2$CH$_2$CH$_2$O)$_{20-200}$, and (aa)$_t$;

aa is independently at each occurrence an amino acid;

Z is selected from the group: aryl substituted with 0-3 $R^{10}$, $C_{3-10}$ cycloalkyl substituted with 0-3 $R^{10}$, and a 5-10 membered heterocyclic ring system containing 1-4 heteroatoms independently selected from N, S, and O and substituted with 0-3 $R^{10}$;

$R^6$, $R^{6a}$, $R^7$, $R^{7a}$, and $R^8$ are independently selected at each occurrence from the group: H, =O, COOH, SO$_3$H, PO$_3$H, $C_1$-$C_5$ alkyl substituted with 0-3 $R^{10}$, aryl substituted with 0-3 $R^{10}$, benzyl substituted with 0-3 $R^{10}$, and $C_1$-$C_5$ alkoxy substituted with 0-3 $R^{10}$, NHC (=O)$R^{11}$, C(=O)NH$R^{11}$, NHC(=O)NH$R^{11}$, NH$R^{11}$, $R^{11}$, and a bond to an additional component;

$R^{10}$ is independently selected at each occurrence from the group: a bond to $S_f$, COO$R^{11}$, C(=O)NH$R^{11}$, NHC (=O)$R^{11}$, OH, NH$R^{11}$, SO$_3$H, PO$_3$H, —OPO$_3H_2$, —OSO$_3$H, aryl substituted with 0-3 $R^{11}$, $C_{1-5}$ alkyl substituted with 0-1 $R^{12}$, $C_{1-5}$ alkoxy substituted with 0-1 $R^{12}$, and a 5-10 membered heterocyclic ring system containing 1-4 heteroatoms independently selected from N, S, and O and substituted with 0-3 $R^{11}$;

$R^{11}$ is independently selected at each occurrence from the group: H, alkyl substituted with 0-1 $R^{12}$, aryl substituted with 0-1 R$^{12}$, a 5-10 membered heterocyclic ring system containing 1-4 heteroatoms independently selected from N, S, and O and substituted with 0-1 R$^{12}$, C$_{3-10}$ cycloalkyl substituted with 0-1 R$^{12}$, polyalkylene glycol substituted with 0-1 R$^{12}$, carbohydrate substituted with 0-1 R$^{12}$, cyclodextrin substituted with 0-1 R$^{12}$, amino acid substituted with 0-1 R$^{12}$, polycarboxyalkyl substituted with 0-1 R$^{12}$, polyazaalkyl substituted with 0-1 R$^{12}$, peptide substituted with 0-1 R$^{12}$, wherein the peptide is comprised of 2-10 amino acids, 3,6-O-disulfo-B-D-galactopyranosyl, bis(phosphonomethyl)glycine, and a bond to an additional component;

R$^{12}$ is a bond to an additional component;

k is selected from 0, 1, and 2;

h is selected from 0, 1, and 2;

h' is selected from 0, 1, and 2;

g is selected from 0, 1, 2, 3, 4, 5,6, 7, 8, 9, and 10;

g' is selected from 0, 1, 2, 3, 4, 5, 6, 7, 8, 9, and 10;

t' is selected from 0, 1, 2, 3, 4, 5, 6, 7, 8, 9, and 10;

x is selected from 0, 1, 2, 3, 4, and 5;

x' is selected from 0, 1, 2, 3, 4, and 5;

In some embodiments, the additional substituent contained on the nanoparticles includes a chelator for a radionuclide or a metal for X-ray or magnetic resonance imaging. Such chelators include those of the formulas:

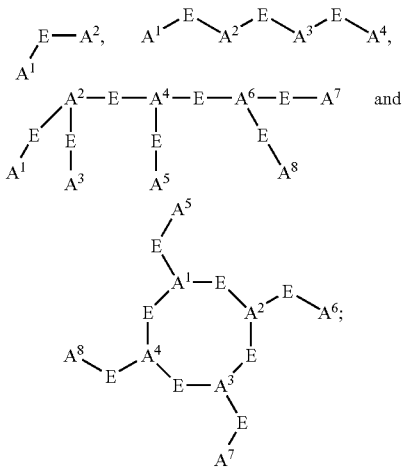

A$^1$, A$^2$, A$^3$, A$^4$, A$^5$, A$^6$, A$^7$, and A$^8$ are independently selected from: NR$^{13}$, NR$^{13}$R$^{14}$, S, SH, S(Pg), O, OH, PR$^{13}$, PR$^{13}$R$^{14}$, P(O)R$^{15}$R$^{16}$, and a bond to the remainder of the complex;

E is a bond, CH, or a spacer group independently selected at each occurrence from the group: C$_1$-C$_{10}$ alkylene substituted with 0-3 R$^{17}$, arylene substituted with 0-3 R$^{17}$, C$_{3-10}$ cycloalkylene substituted with 0-3 R$^{17}$, heterocyclo-C$_{1-10}$ alkylene substituted with 0-3 R$^{17}$, wherein the heterocyclo group is a 5-10 membered heterocyclic ring system containing 1-4 heteroatoms independently selected from N, S, and O, C$_{6-10}$ aryl-C$_{1-10}$ alkyl substituted with 0-3 R$^{17}$, C$_{1-10}$ alkyl-C$_{6-10}$ aryl-substituted with 0-3 R$^{17}$, and a 5-10 membered heterocyclic ring system containing 1-4 heteroatoms independently selected from N, S, and O and substituted with 0-3 R$^{17}$;

R$^{13}$ and R$^{14}$ are each independently selected from the group: a bond to L$_{n'}$, hydrogen, C$_1$-C$_{10}$ alkyl substituted with 0-3 R$^{17}$, aryl substituted with 0-3 R$^{17}$, C$_{1-10}$ cycloalkyl substituted with 0-3 R$^{17}$, heterocyclo-C$_{1-10}$ alkyl substituted with 0-3 R$^{17}$, wherein the heterocyclo group is a 5-10 membered heterocyclic ring system containing 1-4 heteroatoms independently selected from N, S, and O, C$_{6-10}$ aryl-C$_{1-10}$ alkyl substituted with 0-3 R$^{17}$, C$_{1-10}$ alkyl-C$_{6-10}$ aryl-substituted with 0-3 R$^{17}$, a 5-10 membered heterocyclic ring system containing 1-4 heteroatoms independently selected from N, S, and O and substituted with 0-3 R$^{17}$, and an electron, provided that when one of R$^{13}$ or R$^{14}$ is an electron, then the other is also an electron;

alternatively, R$^{13}$ and R$^{14}$ combine to form =C(R$^{20}$)(R$^{21}$);

R$^{15}$ and R$^{16}$ are each independently selected from the group: a bond to L$_{n'}$, —OH, C$_1$-C$_{10}$ alkyl substituted with 0-3 R$^{17}$, C$_1$-C$_{10}$ alkyl substituted with 0-3 R$^{17}$, aryl substituted with 0-3 R$^{17}$, C$_{3-10}$ cycloalkyl substituted with 0-3 R$^{17}$, heterocyclo-C$_{1-10}$ alkyl substituted with 0-3 R$^{17}$, wherein the heterocyclo group is a 5-10 membered heterocyclic ring system containing 1-4 heteroatoms independently selected from N, S, and O, C$_{6-10}$ aryl-C$_{1-0}$ alkyl substituted with 0-3 R$^{17}$, C$_{1-10}$ alkyl-C$_{6-10}$ aryl-substituted with 0-3 R$^{17}$, and a 5-10 membered heterocyclic ring system containing 1-4 heteroatoms independently selected from N, S, and O and substituted with 0-3 R$^{17}$;

R$^{17}$ is independently selected at each occurrence from the group: a bond to L$_{n'}$, =O, F, Cl, Br, I, —CF$_3$, —CN, —CO$_2$R$^{18}$, —C(=O)R$^{18}$, —C(=O)N(R$^{18}$)$_2$, —CHO, —CH$_2$OR$^{18}$, —OC(=O)R$^{18}$, —OC(=O)OR$^{18a}$, —OR$^{18}$, —OC(=O)N(R$^{18}$)$_2$, —NR$^{19}$C(=O)R$^{18}$, —NR$^{19}$C(=O)OR$^{18a}$, —NR$^{19}$C(=O)N(R$^{18}$)$_2$, —NR$^{19}$SO$_2$N(R$^{18}$)$_2$, —NR$^{19}$SO$_2$R$^{18a}$, —SO$_3$H, —SO$_2$R$^{18a}$, —SR$^{18}$, —S(=O)R$^{18a}$, —SO$_2$N(R$^{18}$)$_2$, —N(R$^{18}$)$_2$, —NHC(=S)NHR$^{18}$, =NOR$^{18}$, NO$_2$, —C(=O)NHOR$^{18}$, —C(=O)NHNR$^{18}$R$^{18a}$, —OCH$_2$CO$_2$H, 2-(1-morpholino)ethoxy, C$_1$-C$_5$ alkyl, C$_2$-C$_4$ alkenyl, C$_3$-C$_6$ cycloalkyl, C$_3$-C$_6$ cycloalkylmethyl, C$_2$-C$_6$ alkoxyalkyl, aryl substituted with 0-2 R$^{18}$, and a 5-10 membered heterocyclic ring system containing 1-4 heteroatoms independently selected from N, S, and O;

R$^{18}$, R$^{18a}$, and R$^{19}$ are independently selected at each occurrence from the group: a bond to L$_{n'}$, H, C$_1$-C$_6$ alkyl, phenyl, benzyl, C$_1$-C$_6$ alkoxy, halide, nitro, cyano, and trifluoromethyl;

Pg is a thiol protecting group;

R$^{20}$ and R$^{21}$ are independently selected from the group: H, C$_1$-C$_{10}$ alkyl, —CN, —CO$_2$R$^{25}$, —C(=O)R$^{25}$, —C(=O)N(R$^{25}$)$_2$, C$_2$-C$_{10}$1-alkene substituted with 0-3 R$^{23}$, C$_2$-C$_{10}$ 1-alkyne substituted with 0-3 R$^{23}$, aryl substituted with 0-3 R$^{23}$, unsaturated 5-10 membered heterocyclic ring system containing 1-4 heteroatoms independently selected from N, S, and O and substituted with 0-3 R$^{23}$, and unsaturated C$_{3-10}$ carbocycle substituted with 0-3 R$^{23}$;

alternatively, R$^{20}$ and R$^{21}$, taken together with the divalent carbon radical to which they are attached form:

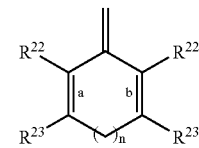

R$^{22}$ and R$^{23}$ are independently selected from the group: H, R$^{24}$, C$_1$-C$_{10}$ alkyl substituted with 0-3 R$^{24}$, C$_2$-C$_{10}$ alkenyl substituted with 0-3 R$^{24}$, C$_2$-C$_{10}$ alkynyl substituted with 0-3 R$^{24}$, aryl substituted with 0-3 R$^{24}$, a 5-10 membered heterocyclic ring system containing 1-4 heteroatoms independently selected from N, S, and O and substituted with 0-3 $R^{24}$, and $C_{3-10}$ carbocycle substituted with 0-3 $R^{24}$;

alternatively, $R^{22}$, $R^{23}$ taken together form a fused aromatic or a 5-10 membered heterocyclic ring system containing 1-4 heteroatoms independently selected from N, S, and O;

a and b indicate the positions of optional double bonds and n is 0 or 1;

$R^{24}$ is independently selected at each occurrence from the group: =O, F, Cl, Br, I, —$CF_3$, —CN, —$CO_2R^{25}$, —C(=O)$R^{25}$, —C(=O)N($R^{25}$)$_2$, —N($R^{25}$)$_3^+$, —$CH_2OR^{25}$, —OC(=O)$R^{25}$, —OC(=O)O$R^{25a}$, —O$R^{25}$, —OC(=O)N($R^{25}$)$_2$, —N$R^{26}$C(=O)$R^{25}$, —N$R^{26}$C(=O)O$R^{25a}$, —N$R^{26}$C(=O)N($R^{25}$)$_2$, —N$R^{26}SO_2$N($R^{25}$)$_2$, —N$R^{26}SO_2R^{25a}$, —$SO_3H$, —$SO_2R^{25a}$, —$SR^{25}$, —S(=O)$R^{25a}$, —$SO_2$N($R^{25}$)$_2$, —N($R^{25}$)$_2$, =NO$R^{25}$, —C(=O)NHO$R^{25}$, —O$CH_2CO_2H$, and 2-(1-morpholino)ethoxy; and, $R^{25}$, $R^{25a}$, and $R^{26}$ are each independently selected at each occurrence from the group: hydrogen and $C_1$-$C_6$ alkyl;

and a pharmaceutically acceptable salt thereof.

In embodiment of the invention the $\alpha_v\beta_3$ targeting moiety may be:

3-[7-[(imidazolin-2-ylamino)methyl]-1-methyl-6,8-difluoroquinoline-4-one-3-ylcarbonylamino]-2-(3,5-dimethylisoxazol-4-ylsulfonylamino)propionic acid, 3-[7-[(imidazolin-2-ylamino)methyl]-1-methyl-6,8-difluoroquinoline-4-one-3-ylcarbonylamino]-2-(benzyloxycarbonylamino)propionic acid, 3-[7-[(imidazolin-2-ylamino)methyl]-1-methyl-6,8-difluoroquinoline-4-one-3-ylcarbonylamino]-2-(n-butyloxycarbonylamino)propionic acid, 3-[7-[(imidazolin-2-ylamino)methyl]-1-methyl-6,8-difluoroquinoline-4-one-3-ylcarbonylamino]-2-(n-butylsulfonylamino)propionic acid, 3-[7-[(tetrahydropyrimid-2-ylamino)methyl]-1-methyl-6,8-difluoroquinoline-4-one-3-ylcarbonylamino]-2-(benzyloxycarbonylamino)propionic acid, 3-[7-[(tetrahydropyrimid-2-ylamino)methyl]-1-methyl-6,8-difluoroquinoline-4-one-3-ylcarbonylamino]-2-(n-butyloxycarbonylamino)propionic acid, 3-[7-[(tetrahydropyrimid-2-ylamino)methyl]-1-methyl-6,8-difluoroquinoline-4-one-3-ylcarbonylamino]-2-(phenylsulfonylamino)propionic acid, 3-[7-[(tetrahydropyrimid-2-ylamino)methyl]-1-methyl-6,8-difluoroquinoline-4-one-3-ylcarbonylamino]-2-(n-butylsulfonyl)aminopropionic acid, 3-[7-[(2-aminothiazol-4-yl)methyl]-1-methyl-6,8-difluoroquinoline-4-one-3-ylcarbonylamino]-2-(benzyloxycarbonylamino)propionic acid, 3-[7-[(imidazolin-2-ylamino)methyl]-1-methyl-6,8-difluoroquinoline-4-one-3-ylcarbonylamino]-2-((2,4,6-trimethylphenyl)sulfonylamino)propionic acid, 3-[7-[(tetrahydropyrimid-2-ylamino)methyl]-1-methyl-6,8-difluoroquinoline-4-one-3-ylcarbonylamino]-2-((2,4,6-trimethylphenyl)sulfonylamino)propionic acid, 3-[7-[(imidazol-2-ylamino)methyl]-1-methyl-6,8-difluoroquinoline-4-one-3-ylcarbonylamino]-2-(3,5-dimethylisoxazol-4-ylsulfonylamino)propionic acid, 3-[7-[(imidazol-2-ylamino)methyl]-1-methyl-6,8-difluoroquinoline-4-one-3-ylcarbonylamino]-2-(benzyloxycarbonylamino)propionic acid, 3-[7-[(imidazol-2-ylamino)methyl]-1-methyl-6,8-difluoroquinoline-4-one-3-ylcarbonylamino]-2-((2,4,6-trimethylphenyl)sulfonylamino)propionic acid, 3-[7-[(imidazol-2-ylamino)methyl]-1-methyl-6,8-difluoroquinoline-4-one-3-ylcarbonylamino]-2-((4-biphenyl)sulfonylamino)propionic acid, 3-[7-[(imidazol-2-ylamino)methyl]-1-methyl-6,8-difluoroquinoline-4-one-3-ylcarbonylamino]-2-(1-naphthylsulfonylamino)propionic acid, 3-[7-[(benzimidazol-2-ylamino)methyl]-1-methyl-6,8-difluoroquinoline-4-one-3-ylcarbonylamino]-2-((2,4,6-trimethylphenyl)sulfonylamino)propionic acid, 3-[7-[(4-methylimidazol-2-ylamino)methyl]-1-methyl-6,8-difluoroquinoline-4-one-3-ylcarbonylamino]-2-((2,4,6-trimethylphenyl)sulfonylamino)propionic acid, 3-[7-[(4,5-dimethylimidazol-2-ylamino)methyl]-1-methyl-6,8-difluoroquinoline-4-one-3-ylcarbonylamino]-2-((2,4,6-trimethylphenyl)sulfonylamino)propionic acid, 3-[7-[(4,5,6,7-tetrahydrobenzimidazol-2-ylamino)methyl]-1-methyl-6,8-difluoroquinoline-4-one-3-ylcarbonylamino]-2-((2,4,6-trimethylphenyl)sulfonylamino)propionic acid, 3-[7-[(pyridin-2-ylamino)methyl]-1-methyl-6,8-difluoroquinoline-4-one-3-ylcarbonylamino]-2-((2,4,6-trimethylphenyl)sulfonylamino)propionic acid, 3-[7-(2-aminopyridin-6-yl)-1-methyl-6,8-difluoroquinoline-4-one-3-ylcarbonylamino]-2-((2,4,6-trimethylphenyl)sulfonylamino)propionic acid, 3-[7-[(7-azabenzimidazol-2-yl)methyl]-1-methyl-6,8-difluoroquinoline-4-one-3-ylcarbonylamino]-2-((2,4,6-trimethylphenyl)sulfonylamino)propionic acid, 3-[7-[(benzimidazol-2-ylamino)methyl]-1-(2-phenylethyl)-6,8-difluoroquinoline-4-one-3-ylcarbonylamino]pro-pionic acid, 3-[7-[(pyridin-2-ylamino)methyl]-1-(2-phenylethyl)-6,8-difluoroquinoline-4-one-3-ylcarbonylamino]propionic acid, 3-[7-[(imidazolin-2-ylamino)methyl]-1-(2-phenylethyl)-6,8-difluoroquinoline-4-one-3-ylcarbonylamino]propionic acid, 3-[7-[(imidazol-2-ylamino)methyl]-1-(2-phenylethyl)-6,8-difluoroquinoline-4-one-3-ylcarbonylamino]propionic acid, 3-[7-[(imidazolin-2-ylamino)methyl]-1-(2-phenylethyl)-6,8-difluoroquinoline-4-one-3-ylcarbonylamino]-2-(benzyloxycarbonylamino)propionic acid, 3-[7-[(imidazolin-2-ylamino)methyl]-1-(2-phenylethyl)-6,8-difluoroquinoline-4-one-3-ylcarbonylamino]-2-(n-butyloxycarbonylamino)propionic acid, 3-[7-[(imidazolin-2-ylamino)methyl]-1-(2-phenylethyl)-6,8-difluoroquinoline-4-one-3-ylcarbonylamino]-2-(phenylsulfonylamino)propionic acid, 3-[7-[(imidazolin-2-ylamino)methyl]-1-(2-phenylethyl)-6,8-difluoroquinoline-4-one-3-ylcarbonylamino]-2-(n-butylsulfonylamino)propionic acid, 3-[7-[(tetrahydropyrimid-2-ylamino)methyl]-1-(2-phenylethyl)-6,8-difluoroquinoline-4-one-3-ylcarbonylamino]-2-(benzyloxycarbonylamino)propionic acid, 3-[7-[(tetrahydropyrimid-2-ylamino)methyl]-1-(2-phenylethyl)-6,8-difluoroquinoline-4-one-3-ylcarbonylamino]-2-(n-butyloxycarbonylamino)propionic acid, 3-[7-[(tetrahydropyrimid-2-ylamino)methyl]-1-(2-phenylethyl)-6,8-difluoroquinoline-4-one-3-ylcarbonylamino]-2-(phenylsulfonylamino)propionic acid, 3-[7-[(tetrahydropyrimid-2-ylamino)methyl]-1-(2-phenylethyl)-6,8-difluoroquinoline-4-one-3-ylcarbonylamino]-2-(n-butylsulfonyl)aminopropionic acid, 3-[7-[(2-aminothiazol-4-yl)methyl]-1-(2-phenylethyl)-6,8-difluoroquinoline-4-one -3-ylcarbonylamino]-2-(phenylsulfonylamino)propionic acid, 3-[7-[(2-aminothiazol-4-yl)methyl]-1-(2-phenylethyl)-6,8-difluoroquinoline-4-one -3-ylcarbonylamino]-2-(benzyloxycarbonylamino)propionic acid, 37[7-[(imidazolin-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(tetrahydropyrimid-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(imidazol-2-ylamino)methyl]-1-(2-phenylethyl)-6,8-difluoroquinoline-4-one-3-ylcarbonylamino]-2-(benzyloxycarbonylamino)propionic acid, 3-[7-[(imidazol-2-ylamino)methyl]-1-(2-phenylethyl)-6,8-difluoroquinoline-4-one-3-ylcarbonylamino]-2-(phenylsulfonylamino)propionic acid, 3-[7-[(imidazol-2-ylamino)methyl]-1-(2-phenylethyl)-6,8-difluoroquinoline-4-one-3-ylcarbonylamino]-2-((2,6,dichlorophenyl)sulfonylamino)propionic acid, 3-[7-[(imidazol-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(imidazol-2-ylamino)methyl]-1-(2-phenylethyl)-6,8-difluoroquinoline-4-one-3-ylcarbonylamino]-2-((4-biphenyl)sulfonylamino)propionic acid, 3-[7-[(benzimidazol-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(4-methylimidazol-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(4,5-dimethylimidazol-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(4,5,6,7-tetrahydrobenzimidazol-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(pyridin-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-(2-aminopyridin-6-yl)-1-(2-phenylethyl)-6,8-difluoroquinoline-4-one-3-ylcarbonylamino]-2-((2,4,6-trimethylphenyl)sulfonylamino)propionic acid, or 3-[7-[(7-azabenzimidazol-2-yl)methyl]-1-(2-phenylethyl)-6,8-difluoroquinoline-4-one-ylcarbonylamino]-2-((2,4,6-trimethylphenyl)sulfonylamino)propionic acid.

Preparation Methods

In a typical procedure for preparing the emulsions of the invention, the fluorochemical liquid and the components of the lipid/surfactant coating are fluidized in aqueous medium to form an emulsion. The functional components of the surface layer may be included in the original emulsion, or may later be covalently coupled to the surface layer subsequent to the formation of the nanoparticle emulsion. In one particular instance, for example, where a nucleic acid targeting agent or drug is to be included, the coating may employ a cationic surfactant and the nucleic acid adsorbed to the surface after the particle is formed.

When appropriately prepared, the nanoparticles that comprise ancillary agents contain a multiplicity of functional such agents at their outer surface, the nanoparticles typically contain hundreds or thousands of molecules of the biologically active agent, targeting ligand, radionuclide and/or MRI contrast agent. For MRI contrast agents, the number of copies of a component to be coupled to the nanoparticle is typically in excess of 5,000 copies per particle, more preferably 10,000 copies per particle, still more preferably 30,000, and still more preferably 50,000-100,000 or more copies per particle. The number of targeting agents per particle is typically less, of the order of several hundred while the concentration of fluorophores, radionuclides, and biologically active agents is also variable.

The nanoparticles need not contain an ancillary agent. In general, the targeted particles, directly coupled to a $\alpha_v\beta_3$-specific ligand, are useful themselves as ultrasound contrast agents. Further, because the particles have a fluorocarbon core, $^{19}$F magnetic resonance imaging can be used to track the location of the particles concomitantly with their additional functions described above. However, the inclusion of other components in multiple copies renders them useful in other respects. For instance, the inclusion of a chelating agent containing a paramagnetic ion makes the emulsion useful as a magnetic resonance imaging contrast agent. The inclusion of biologically active materials makes them useful as drug delivery systems. The inclusion of radionuclides makes them useful either as therapeutic for radiation treatment or as diagnostics for imaging. Other imaging agents include fluorophores, such as fluorescein or dansyl. Biologically active agents may be included. A multiplicity of such activities may be included; thus, images can be obtained of targeted tissues at the same time active substances are delivered to them.

The emulsions can be prepared in a range of methods depending on the nature of the components to be included in the coating. In a typical procedure, used for illustrative purposes only, the following procedure is set forth: Perfluorooctylbromide (40% w/v, PFOB, 3M), and a surfactant co-mixture (2.0%, w/v) and glycerin (1.7%, w/v) is prepared where the surfactant co-mixture includes 64 mole % lecithin (Pharmacia Inc), 35 mole % cholesterol (Sigma Chemical Co.) and 1 mole % dipalmitoyl-L-alpha-phosphatidyl-ethanolamine, Pierce Inc.) dissolved in chloroform. A drug is suspended in methanol (~25 µg/20 µl) and added in titrated amounts between 0.01 and 5.0 mole % of the 2% surfactant layer, preferably between 0.2 and 2.0 mole %. The chloroform-lipid mixture is evaporated under reduced pressure, dried in a 50° C. vacuum oven overnight and dispersed into water by sonication. The suspension is transferred into a blender cup (Dynamics Corporation of America) with perfluorooctylbromide in distilled or deionized water and emulsified for 30 to 60 seconds. The emulsified mixture is transferred to a Microfluidics emulsifier (Microfluidics Co.) and continuously processed at 20,000 PSI for three minutes. The completed emulsion is vialed, blanketed with nitrogen and sealed with stopper crimp seal until use. A control emulsion can be prepared identically excluding the drug from the surfactant commixture. Particle sizes are determined in triplicate at 37° C. with a laser light scattering submicron particle size analyzer (Malvern Zetasizer 4, Malvern Instruments Ltd., Southborough, Mass.), which indicate tight and highly reproducible size distribution with average diameters less than 400 nm. Unincorporated drug can be removed by dialysis or ultrafiltration techniques. To provide the targeting ligand, an $\alpha_v\beta_3$ ligand is coupled covalently to the phosphatidyl ethanolamine through a bifunctional linker in the procedure described above.

Kits

The emulsions of the invention may be prepared and used directly in the methods of the invention, or the components of the emulsions may be supplied in the form of kits. The kits may comprise the pre-prepared targeted composition containing all of the desired ancillary materials in buffer or in lyophilized form. Alternatively, the kits may include a form of the emulsion which lacks the $\alpha_v\beta_3$ ligand which is supplied separately. Under these circumstances, typically, the emulsion will contain a reactive group, such as a maleimide group, which, when the emulsion is mixed with the targeting agent, effects the binding of the targeting agent to the emulsion itself. A separate container may also provide additional reagents useful in effecting the coupling. Alternatively, the emulsion may contain reactive groups which bind to linkers coupled to the desired component to be supplied separately which itself contains a reactive group. A wide variety of approaches to constructing an appropriate kit may be envisioned. Individual components which make up the ultimate emulsion may thus be supplied in separate containers, or the kit may simply contain reagents for combination with other materials which are provided separately from the kit itself.

A non-exhaustive list of combinations might include: emulsion preparations that contain, in their lipid-surfactant layer, an ancillary component such as a fluorophore or chelating agent and reactive moieties for coupling to the $\alpha_v\beta_3$ targeting agent; the converse where the emulsion is coupled to targeting agent and contains reactive groups for coupling to an ancillary material; emulsions which contain both targeting agent and a chelating agent but wherein the metal to be chelated is either supplied in the kit or independently provided by the user; preparations of the nanoparticles comprising the surfactant/lipid layer where the materials in the lipid layer contain different reactive groups, one set of reactive groups for a $\alpha_v\beta_3$ ligand and another set of reactive groups for an ancillary agent; preparation of emulsions containing any of the foregoing combinations where the reactive groups are supplied by a linking agent.

Applications

The emulsions and kits for their preparation are useful in the methods of the invention which include imaging of tissues containing high expression levels of $\alpha_v\beta_3$ integrin, and where tissues with such expression levels are undesirable, treatment. High expression levels of $\alpha_v\beta_3$ are typical of activated endothelial cells and are considered diagnostic for neovasculature.

The diagnostic radiopharmaceuticals are administered by intravenous injection, usually in saline solution, at a dose of 1 to 100 mCi per 70 kg body weight, or preferably at a dose of 5 to 50 mCi. Imaging is performed using known procedures.

The therapeutic radiopharmaceuticals are administered by intravenous injection, usually in saline solution, at a dose of 0.01 to 5 mCi per kg body weight, or preferably at a dose of 0.1 to 4 mCi per kg body weight. For comparable therapeutic radiopharmaceuticals, current clinical practice sets dosage ranges from 0.3 to 0.4 mCi/kg for Zevalin™ to 1-2 mCi/kg for OctreoTher™, a labeled somatostatin peptide. For such therapeutic radiopharmaceuticals, there is a balance between tumor cell kill vs. normal organ toxicity, especially radiation nephritis. At these levels, the balance generally favors the tumor cell effect. These dosages are higher than corresponding imaging isotopes.

The magnetic resonance imaging contrast agents of the present invention may be used in a similar manner as other MRI agents as described in U.S. Pat. No. 5,155,215; U.S. Pat. No. 5,087,440; Margerstadt, et al., *Magn. Reson. Med.* (1986) 3:808; Runge, et al., *Radiology* (1988) 166:835; and Bousquet, et al., *Radiology* (1988) 166:693. Other agents that may be employed are those set forth in U.S. patent publication 2002/0,127,182 which are pH sensitive and can change the contrast properties dependent on pulse. Generally, sterile aqueous solutions of the contrast agents are administered to a patient intravenously in dosages ranging from 0.01 to 1.0 mmoles per kg body weight.

A particularly preferred set of MRI chelating agents includes 1,4,7,10-tetraazacyclododecane-1,4,7,10-tetraacetic acid (DOTA) and its derivatives, in particular, a methoxybenzyl derivative (DOTA-NCS) comprising an isothiocyanate functional group which can then be coupled to the amino group of phosphatidyl ethanolamine or to a peptide derivatized form thereof. Derivatives of this type are described in U.S. Pat. No. 5,573,752, incorporated herein by reference. Other suitable chelating agents are disclosed in U.S. Pat. No. 6,056,939, also incorporated herein by reference.

The DOTA isocyanate derivative can also be coupled to the lipid/surfactant directly or through a peptide spacer. The use of gly-gly-gly as a spacer is illustrated in the reaction scheme below. For direct coupling, the DOTA-NCS is simply reacted with PE to obtain the coupled product. When a peptide is employed, for example a triglycyl link, phosphoethanolamine (PE) is first coupled to t-boc protected triglycine. Standard coupling techniques, such as forming the activated ester of the free acid of the t-boc-triglycine using diisopropyl carbodiimide (or an equivalent thereof) with either N-hydroxy succinimide (NHS) or hydroxybenzotriazole (HBT) are employed and the t-boc-triglycine-PE is purified.

Treatment of the t-boc-triglycine-PE with trifluoroacetic acid yields triglycine-PE, which is then reacted with excess DOTA-NCS in DMF/CHCl$_3$ at 50° C. The final product is isolated by removing the solvent, followed by rinsing the remaining solid with excess water, to remove excess solvent and any un-reacted or hydrolyzed DOTA-NCS.

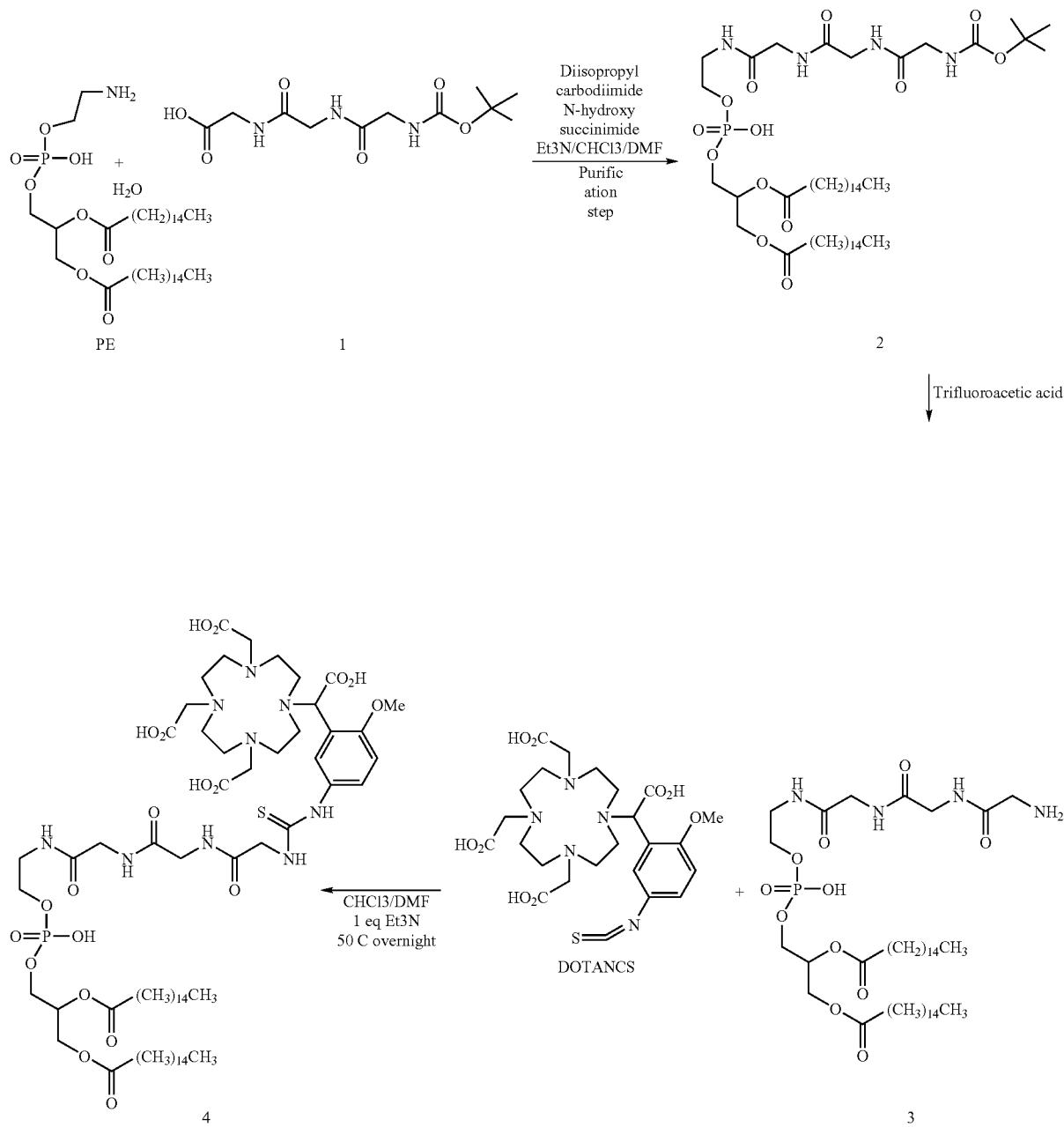

For use as X-ray contrast agents, the compositions of the present invention should generally have a heavy atom concentration of 1 mM to 5 M, preferably 0.1 M to 2 M. Dosages, administered by intravenous injection, will typically range from 0.5 mmol/kg to 1.5 mmol/kg, preferably 0.8 mmol/kg to 1.2 mmol/kg. Imaging is performed using known techniques, preferably X-ray computed tomography.

The ultrasound contrast agents of the present invention are administered by intravenous injection in an amount of 10 to 30 μL of the echogenic gas per kg body weight or by infusion at a rate of approximately 3 μL/kg/min. Imaging is performed using known techniques of sonography.

The methods of employing the nanoparticulate emulsions of the invention are well known to those in the art. Typically, the tissues of interest to be imaged or treated include areas of inflammation, which may characterize a variety of disorders including rheumatoid arthritis, areas of irritation such as those affected by angioplasty resulting in restenosis, tumors, and areas affected by atherosclerosis.

The following examples are offered to illustrate but not to limit the invention.

Preparation A

Part A—DSPE-PEG(2000)Maleimide-Mercaptoacetic Acid Adduct

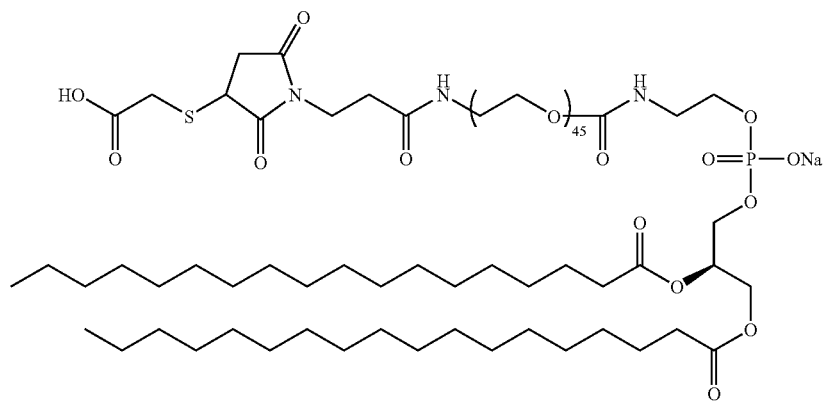

1,2-Distearoyl-sn-Glycero-3-Phosphoethanolamine-N-[Maleimide(Polyethylene Glycol)2000] is dissolved in DMF and degassed by sparging with nitrogen or argon. The oxygen-free solution is adjusted to pH 7-8 using DIEA, and treated with mercaptoacetic acid. Stirring is continued at ambient temperatures until analysis indicates complete consumption of starting materials. The solution is used directly in the following reaction.

Part B—Conjugation of the DSPE-PEG(2000)Maleimide-Mercaptoacetic Acid Adduct With 2-[({4-[3-(N-{2-[(2R)-2-((2R)-2-Amino-3-sulfopropyl)-3-sulfopropyl]ethyl}carbamoyl)propoxyl]-2,6-dimethylphenyl}sulfonyl)aminol](2S)-3-({7-[(imidazol-2-ylamino)methyl]-1-methyl-4-oxo(3-hydroquinoly)}carbonylamino)propanoic acid

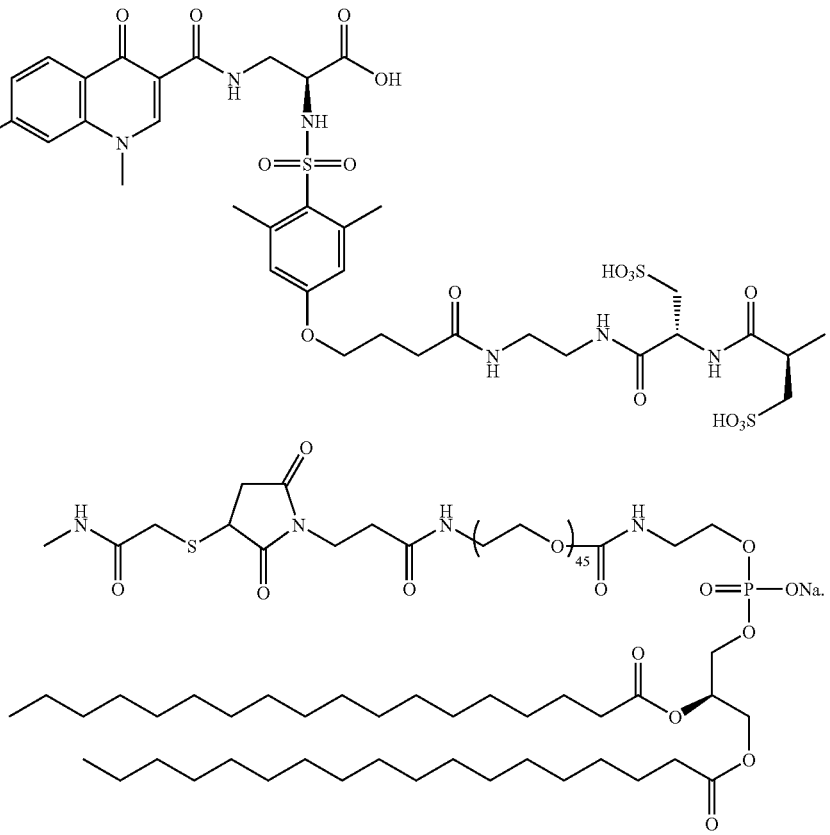

The product solution of Part A, above, is pre-activated by the addition of HBTU and sufficient DIEA to maintain pH 8-9. To the solution is added 2-[({4-[3-(N-{2-[(2R)-2-amino-3-sulfopropyl)-3-sulfopropyl]ethyl}carbamoyl)propoxy]-2,6-dimethylphenyl}sulfonyl)amino](2S)-3-({7-[(imidazol-2-ylamino)methyl]-1-methyl-4-oxo(3-hydroquinolyl)}carbonylamino)propanoic acid, and the solution is stirred at room temperature under nitrogen for 18 h. DMF is removed in vacuo and the crude product is purified by preparative HPLC to obtain the Part B title compound.

EXAMPLE 1

Tumor Imaging

A. Tumor Model and Preparation of Nanoparticles:

Male New Zealand White Rabbits (~2.0 kg) were anesthetized with intramuscular ketamine and xylazine (65 and 13 mg/kg, respectively). The left hind leg of each animal was shaved, sterile prepped and infiltrated locally with Marcaine™ prior to placement of a small incision above the popliteal fossa. A 2 by 2 by 2 mm$^3$ Vx-2 carcinoma tumor fragment, freshly obtained from a donor animal, was implanted at a depth of approximately 0.5 cm. Anatomical planes were reapproximated and secured with a single absorbable suture. Finally, the skin incision was sealed with Dermabond skin glue. Following the tumor implantation procedure, the effects of xylazine were reversed with yohimbine and animals were allowed to recover.

Twelve days after Vx-2 implantation rabbits were anesthetized with 1% to 2% Isoflurane™, intubated, ventilated and positioned within the bore of the MRI scanner for study. Intravenous and intraarterial catheters, placed in opposite ears of each rabbit, were used for systemic injection of nanoparticles and arterial blood sampling as described below. Animals were monitored physiologically throughout the study in accordance with a protocol and procedures approved by the Animal Studies Committee at Washington University Medical School.

At 12 days post-implantation, Vx-2 tumor volumes of animals receiving the $\alpha_v\beta_3$-targeted (130±39 mm$^3$) or non-targeted nanoparticles (148±36 mm$^3$) were not different (p>0.05).

Twelve New Zealand rabbits implanted with Vx-2 tumors, as described above, were randomized into three treatment regimens and received either:
1) $\alpha_v\beta_3$-integrin-targeted paramagnetic nanoparticles ($\alpha_v\beta_3$-targeted, n=4),
2) non-targeted paramagnetic nanoparticles (i.e., control group, n=4), or
3) $\alpha_v\beta_3$-integrin-targeted non-paramagnetic nanoparticles followed by $\alpha_v\beta_3$-integrin targeted paramagnetic nanoparticles (i.e., competition group, n=4).

In treatment groups 1 and 2, rabbits received 0.5 ml/kg of $\alpha_v\beta_3$-integrin-targeted or control paramagnetic nanoparticles following the acquisition of baseline MR images. In treatment group 3, all rabbits received 0.5 ml/kg $\alpha_v\beta_3$-integrin-targeted non-paramagnetic nanoparticles two hours before MR imaging followed by 0.5 ml/kg $\alpha_v\beta_3$-integrin-targeted paramagnetic nanoparticles. Dynamic MR images were obtained at injection and every 30 minutes for each animal over two hours to monitor initial changes in signal enhancement in the tumor and muscle regions. All tumors were resected and frozen for histology to corroborate MR molecular imaging results.

The paramagnetic nanoparticles were produced as described in Flacke, S., et al., *Circulation* (2001) 104:1280-1285. Briefly, the nanoparticulate emulsions were comprised of 40% (v/v) perfluorooctylbromide (PFOB), 2% (w/v) of a surfactant co-mixture, 1.7% (w/v) glycerin and water representing the balance.

The surfactant of control, i.e., non-targeted, paramagnetic emulsions included 60 mole % lecithin (Avanti Polar Lipids, Inc., Alabaster, Ala.), 8 mole % cholesterol (Sigma Chemical Co., St. Louis, Mo.), 2 mole % dipalmitoyl-phosphatidylethanolamine (DPPE) (Avanti Polar Lipids, Inc., Alabaster, Ala.) and 30 mole % gadolinium diethylenetriaminepentaacetic acid-bisoleate (Gd-DTPA-BOA, Gateway Chemical Technologies, St. Louis, Mo.). The preparation of Gd-DTPA-BOA is described by Cacheris, W. P., et al., U.S. Pat. Nos. 5,571,498 and 5,614,170, both incorporated herein by reference.

$\alpha_v\beta_3$-targeted paramagnetic nanoparticles were prepared as above with a surfactant co-mixture that included: 60 mole % lecithin, 0.05 mole % N-[{w-[4-(p-maleimidophenyl)butanoyl]amino} poly(ethylene glycol)2000]1,2-distearoyl-sn-glycero-3-phosphoethanolamine (MPB-PEG-DSPE) covalently coupled to the $\alpha_v\beta_3$-integrin peptidomimetic antagonist (Bristol-Myers Squibb Medical Imaging, Inc., North Billerica, Mass.), 8 mole % cholesterol, 30 mole % Gd-DTPA-BOA and 1.95 mole % DPPE.

$\alpha_v\beta_3$-targeted non-paramagnetic nanoparticles were prepared in an identical fashion to the targeted formulation excluding the addition of a lipophilic Gd$^{3+}$ chelate, which was substituted in the surfactant co-mixture with increased lecithin (70 mole %) and cholesterol (28 mole %).

The components for each nanoparticle formulation were emulsified in a M110S Microfluidics emulsifier (Microfluidics, Newton, Mass.) at 20,000 PSI for four minutes. The completed emulsions were placed in crimp-sealed vials and blanketed with nitrogen.

Particle sizes were determined at 37° C. with a laser light scattering submicron particle size analyzer (Malvern Instruments, Malvern, Worcestershire, UK) and the concentration of nanoparticles was calculated from the nominal particle size (i.e., particle volume of a sphere). The particle size distribution is shown in FIG. 1—most of the particles had diameters less than 400 nm.

Perfluorocarbon concentration was determined with gas chromatography using flame ionization detection (Model 6890, Agilent Technologies, Inc., Wilmington, Del.). One ml of perfluorocarbon emulsion combined with 10% potassium hydroxide in ethanol and 2.0 ml of internal standard (0.1% octane in Freon@) was vigorously vortexed then continuously agitated on a shaker for 30 minutes. The lower extracted layer was filtered through a silica gel column and stored at 4-6° C. until analysis. Initial column temperature was 30° C. and ramped upward at 10° C./min to 145° C.

The gadolinium content of the emulsions was determined by neutron activation analysis in a 300 kW nuclear reactor (Landsberger, S., *Chemical Analysis by Nuclear Methods*, pp. 122-140, Z. B. Alfassi (ed.), New York: Wiley (1994)). The number of Gd$^{3+}$ complexes per nanoparticle was calculated from the ratio of the concentrations of Gd$^{3+}$ and the estimated number of nanoparticles in the emulsion. In addition, the relaxivities of each paramagnetic nanoparticle formulation were measured at 0.47 Tesla and 40° C. with a Minispec Analyzer (Bruker, Inc., Milton, ON, Canada).

The characteristics of the particles are shown in Table 1.

Concentrations are reported relative to the total emulsion volume in liters. Relaxivity values ($r_1$ and $r_2$) were determined at 0.47 Tesla and calculated relative to [Gd$^{3+}$] or [nanoparticles] as indicated.

TABLE 1

Physical and Chemical Characteristics of $\alpha_v\beta_3$-Targeted and Non-Targeted Nanoparticles

|  | $\alpha_v\beta_3$-targeted | Non-targeted |
|---|---|---|
| Particle Size (nm) | 273 | 263 |
| Polydispersity Index | 0.15 | 0.21 |
| [$Gd^{3+}$] (mM) | 6.19 | 6.77 |
| [$^{19}F$] (M) | 28.9 | 28.6 |
| [Particles] (nM) | 65.5 | 73.3 |
| $Gd^{3+}$ Ions/Particle | 94,400 | 92,400 |
| $r_1$ (s*mM)$^{-1}$ [Gd] | 19.1 | 21.1 |
| $r_2$ (s*mM)$^{-1}$ [Gd] | 22.9 | 24.6 |
| $r_1$ (s*mM)$^{-1}$ [Particle] | 1,800,000 | 1,950,000 |
| $r_2$ (s*mM)$^{-1}$ [Particle] | 2,160,000 | 2,270,000 |

B. Magnetic Resonance Imaging and Histology Procedures

Twelve days after tumor implantation, the animals underwent MRI scanning on a 1.5 Tesla clinical scanner (NT Intera with Master Gradients, Philips Medical Systems, Best, Netherlands). Each animal was placed inside a quadrature head/neck birdcage coil with an 11 cm diameter circular surface coil positioned against the hindlimb near the tumor. The quadrature body coil was used for all radio-frequency transmission; the birdcage coil was used for detection during scout imaging; and the surface coil was used for detection during high-resolution imaging. A 10 ml syringe filled with gadolinium diethylenetriaminepentaacetic acid (Gd-DTPA) doped water was placed within the high-resolution field of view (FOV) and served as a signal intensity standard.

Tumors were initially localized at the site of implantation with a $T_2$-weighted turbo spin-echo scan (TR: 2000 ms, TE: 100 ms, FOV: 150 mm, slice thickness: 3 mm, matrix: 128 by 256, signal averages: 2, turbo factor: 3, scan time: 3 min). A high-resolution, $T_1$-weighted, fat suppressed, three-dimensional, gradient echo scan (TR: 40 ms, TE: 5.6 ms, FOV: 64 mm, slice thickness: 0.5 mm, contiguous slices: 30, in-plane resolution: 250 μm, signal averages: 2, flip angle: 65°, scan time: 15 min) of the tumor was collected at baseline and repeated immediately and 30, 60, 90 and 120 minutes after paramagnetic nanoparticle injection.

Tumor volumes were calculated on an offline image processing workstation (EasyVision v5.1, Philips Medical Systems, Best, Netherlands). Regions-of-interest (ROI) were applied manually around the tumor in each slice of the $T_1$-weighted baseline scan, were combined into a three-dimensional object and the volume calculated.

To quantify image enhancement over time, an unbiased image analysis program was used. $T_1$-weighted images (three contiguous slices through the center of each tumor) collected before, immediately after and 30, 60, 90 and 120 minutes after intravenous nanoparticle injection were analyzed with MATLAB (The MathWorks, Inc., Natick, Mass.). The image intensity at each timepoint was normalized to the baseline image via the reference gadolinium standard. Serial images were spatially co-registered and contrast enhancement was determined for each pixel at each post-injection timepoint. An ROI was manually drawn around a portion of the hindlimb muscle in the baseline images and the average pixel-by-pixel signal enhancement inside the ROI was calculated at each timepoint. A second ROI was manually drawn around the tumor and the standard deviation of the tumor signal was calculated in the baseline image for each animal. Pixels were considered enhanced when signal intensity was increased by greater than three times the standard deviation of the tumor signal at baseline (i.e., enhancement greater than 99% of the variation seen at baseline). Solitary enhancing pixels, those in which all surrounding in-plane pixels did not enhance, were removed from the calculations as noise. The remaining enhancing pixel clusters were mapped back to the immediate, 30, 60 and 90 minute images and the average signal increase at each interval was determined. Statistical comparisons were performed for tumor and muscle for each timepoint using ANOVA (SAS, SAS Institute, Cary, N.C.). Treatment means were separated using the LSD procedure (p<0.05).

After imaging, tumors were resected for histology and immunohistochemistry to verify tumor pathology and assess associated vascularity and angiogenesis. Tumors were frozen (−78° C.) in OCT medium with known orientation relative to original anatomical position and the MRI image planes. Four micron frozen sections (Leica Microsystems, Inc., Bannockburn, Ill.), fixed in acetone at −20° C. for 15 minutes and air dried overnight (4° C.), were stained with hematoxylin-eosin, murine anti-human/rabbit endothelium antibody (QBEND/40, 1:10 dilution, Research Diagnostics, Inc., Flanders, N.J.), or a murine anti-human $\alpha_v\beta_3$-integrin (LM-609, 1:200 dilution, Chemicon International, Temecula, Calif.). Immunohistochemistry was performed using the Vectastain® Elite ABC kit (Vector Laboratories, Burlingame, Calif. 94010), developed with the Vector® VIP kit, counterstained with Vector® methylgreen nuclear counterstain. Slides were reviewed with a Nikon Eclipse E800 research microscope (Nikon USA, Melville, N.Y.) equipped with a Nikon digital camera (Model DXM 1200) and captured with Nikon ACT-1 software.

Figure 2:
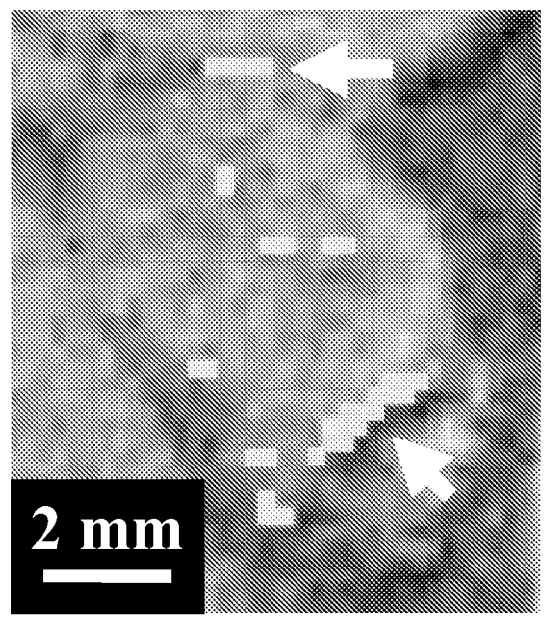
FIG. 2 shows an enlarged section of $T_1$-weighted magnetic resonance image of an implanted Vx-2 tumor.
Figure 3:
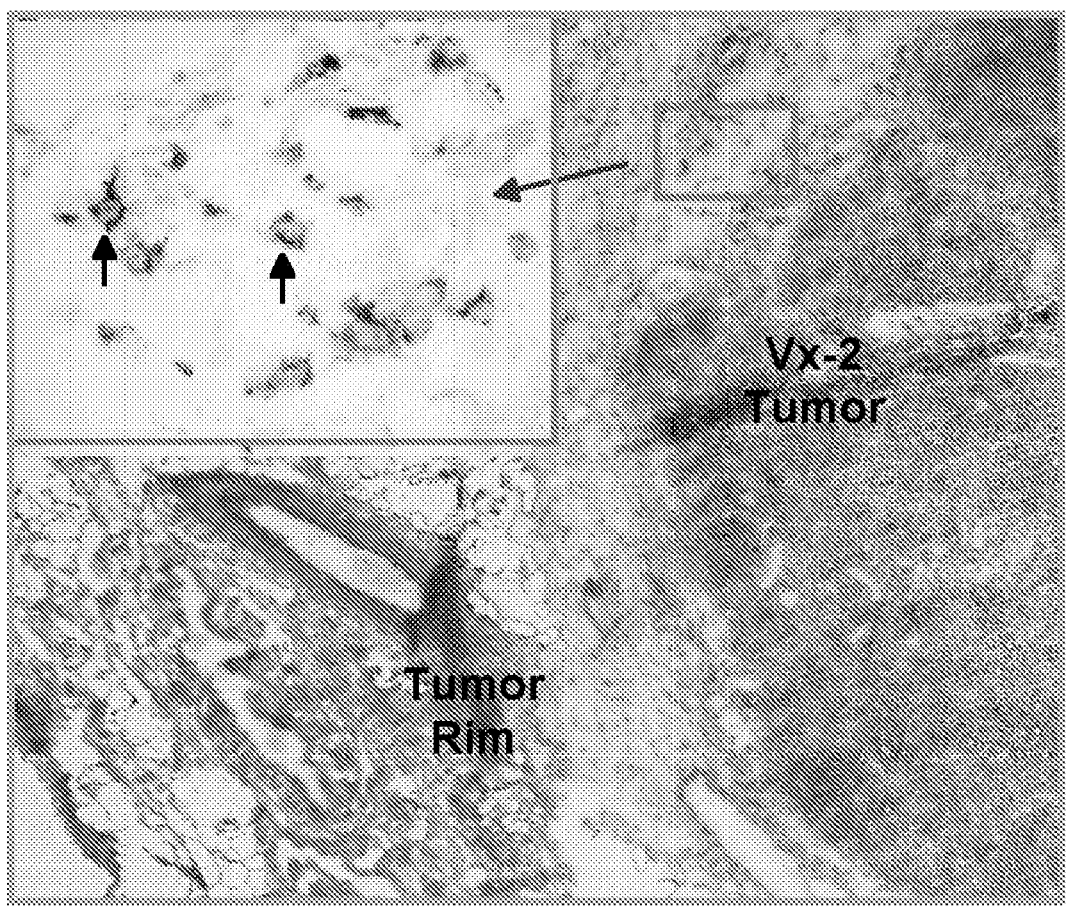
FIG. 3 shows histological sections of Vx-2 tumor with H&E staining (low power magnification) and $\alpha_v\beta_3$ staining (inset, high-power magnification).

C. Results of Imaging and Histology $T_1$-weighted MR images of the Vx-2 tumor rabbits receiving $\alpha_v\beta_3$-targeted paramagnetic nanoparticles revealed a marked increase in MR contrast primarily, although not exclusively, located asymmetrically along the tumor periphery. $\alpha_v\beta_3$-integrin enhancement was typically seen in a patchy distribution adjacent to blood vessels and along tissue fascial interfaces (FIG. 2). Histology and immunocytochemical assessments of the Vx-2 tumors corroborated that angiogenesis was most intensely distributed within a few independent regions along the tumor periphery and found less extensively within intratumoral connective tissue tracts interspersed between tumor cell lobules (FIG. 3).

Figure 4:
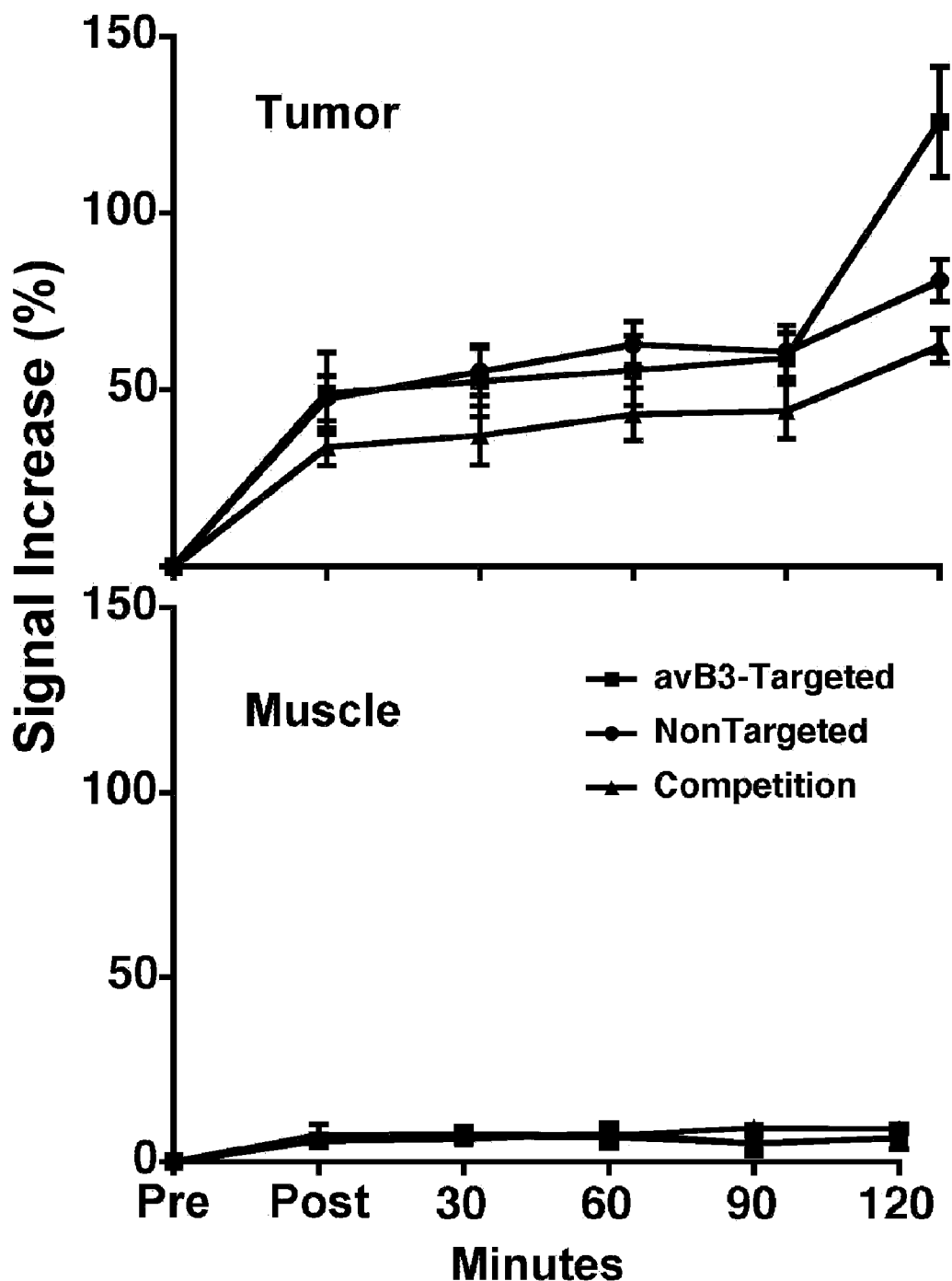
FIG. 4 is a graph showing enhancement in ROI from tumor (top) and muscle (bottom) in subjects receiving either targeted or non-targeted nanoparticles.

Temporally, MRI contrast enhancement provided by $\alpha_v\beta_3$-targeted paramagnetic nanoparticles was detected in regions of angiogenesis soon after injection at relatively low levels, which was presumably attributed to a local extravasation of nanoparticles through a fenestrated neovasculature at 30 minutes (FIG. 4). No intravascular blood pool contrast effect was detectable after 30 minutes. After two hours, the magnitude of signal enhancement among rabbits treated with the $\alpha_v\beta_3$-targeted nanoparticles increased (56%) relative to the non-targeted nanoparticle effect (p<0.05). Blockage of $\alpha_v\beta_3$-integrin sites with pretargeted non-paramagnetic $\alpha_v\beta_3$-nanoparticles two hours before injection of the $\alpha_v\beta_3$-targeted paramagnetic particles reduced the targeted contrast signal enhancement in half (p<0.05), to a signal effect slightly below that attributed to localized neovascular leakage, confirming the specificity of the targeted nanoparticles.

In addition to the tumor capsule, contrast enhancement was shown in a patchy distribution among many of the vessels within the fossa and in particular, within the wall of larger veins located only a few millimeters from capsular regions of angiogenesis. In one example, the magnitude of contrast signal enhancement determined for a venous angiogenic signal in close proximity to the tumor capsular signal increased in parallel over time, suggesting a source and target (data not shown). In many instances, angiogenesis stimulated in nearby vasculature by factors elaborated from the tumor, clearly had not bridged to the tumor by 12 days post-implantation. Examination of the vasculature within the contralateral popliteal fossa revealed no MR signal changes following injection with either $\alpha_v\beta_3$-targeted or non-targeted paramagnetic nanoparticles.

Figure 5:
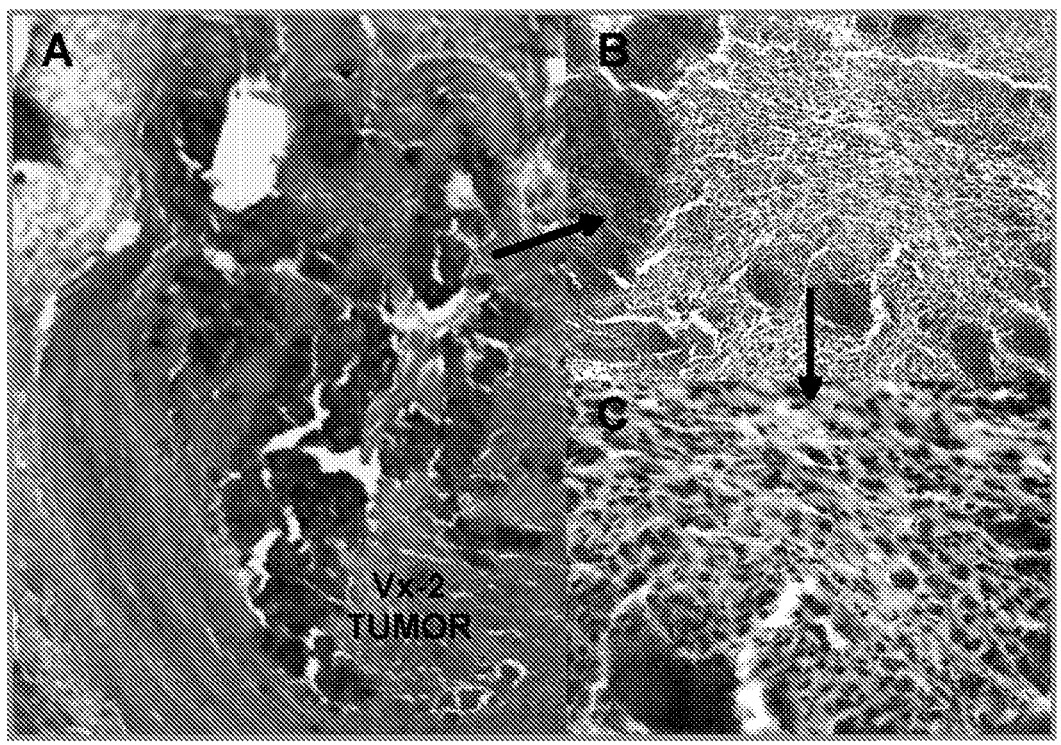
FIGS. 5A-5C show various magnification levels of histological sections of inflammation in tumor slices.

All Vx-2 rabbits routinely underwent baseline $T_2$-weighted MRI imaging at the known site of surgery to localize tumor at 12 days post-implantation. In some rabbits, no tumor was detected and so these were excluded from the study. In a few other animals, a mass which appeared appropriate based upon on size and $T_2$-image characteristics was observed, but later histology revealed it to be a tumor remnant with heavy infiltrates of inflammatory cells (FIG. 5); these animals were excluded from the study as well. The hyperintense appearance on $T_2$-weighted MRI is due to edema associated with inflammation.

Figure 6:
FIG. 6 shows $T_2$-weighted and $T_1$-weighted MRI of tumors targeted with $\alpha_v\beta_3$ targeted nanoparticles.
Figure 6:
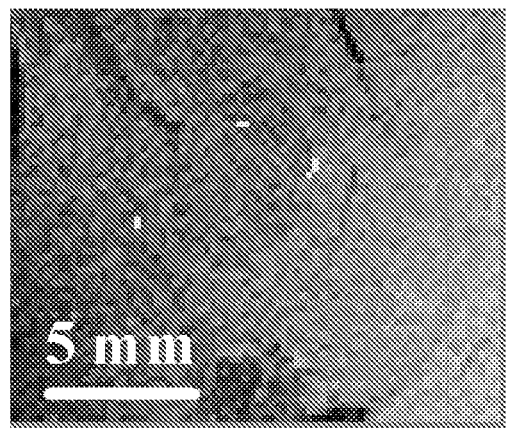

Among this subset of animals, some randomly received $\alpha_v\beta_3$-targeted paramagnetic nanoparticles and no MR contrast enhancement was shown within the periphery of the mass nor within nearby vasculature (FIG. 6). This lack of signal enhancement associated with a popliteal mass or adjacent vasculature was distinct from the molecular imaging features routinely obtained in animals with histologically verified tumor. Histology and immunohistochemical analysis of the remnant tissues confirmed a paucity of vascularity in the tumor periphery and adjacent tissues with negligible staining for the $\alpha_v\beta_3$-integrin. These findings illustrate the specificity of molecular imaging to help differentiate viable Vx-2 masses from tumor remnants.

EXAMPLE 2

Imaging of Atherosclerosis

A. Model System and Nanoparticles

Both targeted and non-targeted nanoparticles were prepared as described in paragraph A of Example 1. The characteristics obtained were similar—the particles contained 6.17 mM Gd, or about 94,200 Gd atoms/particle. The nominal particle size measured by elastic light scattering (Malvern Instruments, Worchestershire, UK) was 273 nm with a "polydispersity index" (or distribution bandwidth) of 0.15.

The actual T1 and T2 relaxivities (r1 and r2, respectively) of the particle formulations were determined with the use of standard inversion recovery pulse sequences and multiecho sequences applied to pure samples (nanoparticles present at 59 nM) placed in a quadrature birdcage coil and imaged with a clinical 1.5T system (Philips NT Intera CV, Philips Medical Systems, Best, Netherlands). The "ionic-based" r1 and $r_2$ values for paramagnetic nanoparticles expressed per mM $Gd^{3+}$ are 17.7±0.2 and 25.3±0.6 $(sec \cdot mM)^{-1}$ respectively. "Particle-based" relaxivities are 1,670,000±100,000 and 2,380,000±120,000 $(sec \cdot mM\ particle)^{-1}$ for r1 and r2. These relaxivities are more than 5 orders of magnitude greater than those for commercially available paramagnetic contrast agents.

The targeted nanoparticles each contained approximately 200-300 copies of the peptidomimetic linked to the particle lipid membrane through the coupled phospholipid, described in Preparation A, part B. Physical characteristics of the nanoparticles were unaffected by the inclusion of the targeting ligand, including pharmacokinetic properties, and both targeted and control particles exhibited indistinguishable paramagnetic properties.

To induce atherosclerosis, 13 male New Zealand White rabbits were fed either 1% cholesterol (n=9) or standard rabbit chow (n=4) for 80 days. The contrast agents were injected intravenously via ear vein in a dose of 0.5 ml/kg body weight; i.e., about $10_{14}$ nanoparticles per dose. Three experimental groups were used:
1) Control diet animals administered $\alpha_v\beta_3$-targeted paramagnetic nanoparticles (n=4);
2) High-cholesterol rabbits administered $\alpha_v\beta_3$-targeted nanoparticles (n=5) or
3) High-cholesterol rabbits administered non-targeted control nanoparticles (n=4).

Following MRI, all aortas extracted for histological assessment. Routine hematoxylin/eosin staining was performed on formalin-fixed, paraffin embedded sections (4?m) of aorta. Expression of $\alpha_v\beta_3$ integrin in the aortic wall was confirmed by immunohistochemistry of formalin-fixed sections with use of a specific primary antibody (LM609: Chemicon International, Inc., Temecula, Calif.), and secondary antibody developed with VIP substrate Kit. PECAM was stained similarly with CD31 primary antibody (Chemicon International, Inc., Temecula, Calif.). Images of neovasculature were digitized under high power (600×) with a Nikon microscope and Nikon DXM1200 camera.

The experimental protocol was approved by the Animal Studies Committee of the Washington University School of Medicine.

B. Imaging and Histology

MR images were obtained in a manner similar to that set forth in paragraph B of Example 1. A 1.5T magnet (NT Intera CV, Philips Medical Systems, Best, Netherlands) was used along with a quadrature birdcage RF receive coil to image the aorta in vivo before and after treatment with paramagnetic nanoparticles. Multislice T1-weighted spin-echo, fat-saturated, black-blood imaging of the aorta was performed from the renal arteries to the diaphragm (TR 380 ms; TE 11 ms; 250 by 250 μm in-plane resolution, 5 mm slice thickness; NSA=8). Although the actual TR used for imaging in vivo was not optimal, according to our signal simulations, it provided a practical means to acquire the data in a short period of time. The effect on signal intensity is best illustrated as having to approximately double the nanoparticle concentration (to around 100 pM) to achieve a CNR=5 at 1.5T. To null the blood signal, "sliding rf" saturation bands were placed proximal and distal to the region of image acquisition and moved with the selected imaging plane.

C. Results of Imaging and Histochemistry

The use of targeted nanoparticles showed enhancement of the contrast image in locations verified as associated with atherosclerosis.

Figure 7:
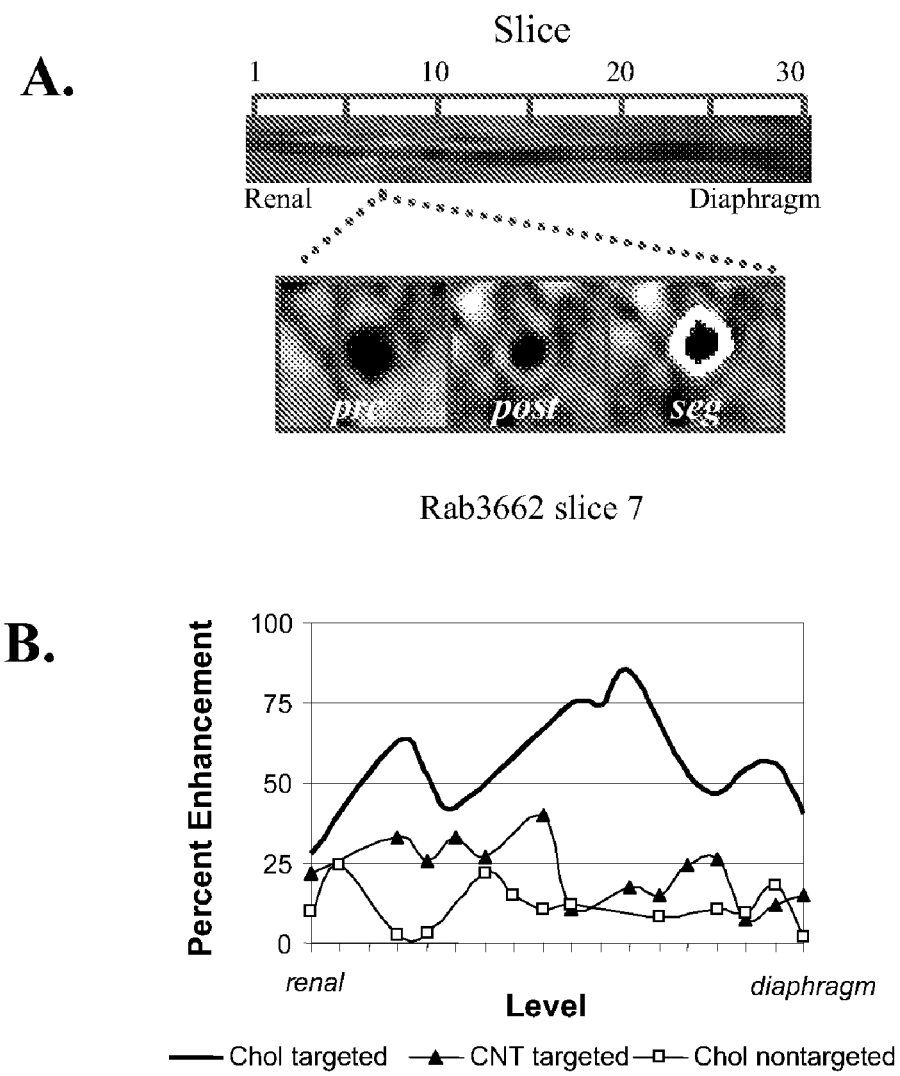
FIG. 7A shows a spin-echo image of aortic slices before and after administration of $\alpha_v\beta_3$ labeled particles.
FIG. 7B shows the enhancement of image in aorta of cholesterol treated subjects, untreated subjects, and in cholesterol treated subjects with non-targeted emulsions.

FIG. 7A (top) shows the imaged portion of the aorta in longitudinal profile for a selected animal and tranverse slices (bottom) before and 120 minutes after treatment with targeted nanoparticles, and also an example of output from a custom-designed image segmentation algorithm for quantitative signal analysis of individual aortic slices. The signal in the aortic wall is increased after contrast injection (middle panel), indicating the presence of targeted nanoparticles that have bound to the $\alpha_v\beta_3$ integrin epitopes. Furthermore, the aortic blood pool background is not confounding (note: low blood signal in lumen) in view of the small doses of nanoparticles used and the "black blood" signal nulling procedure, which enables immediate detection of contrast enhancement in the aortic wall without requiring a waiting period for blood pool clearance of contrast agent.

FIG. 7B shows the variation of contrast enhancement longitudinally along the aorta for three selected rabbits. Overall, greater signal enhancement was observed in the high-cholesterol targeted rabbits at practically all aortic segments. As shown, the percent enhancement with targeted particles in the rabbit fed a high cholesterol diet was markedly higher than either the enhancement of image using non-targeted nanoparticles in a rabbit fed a high cholesterol diet (open squares) and higher than the enhancement using targeted particles in a rabbit fed a normal diet (solid triangles).

Variability of contrast enhancement within the aortic wall was determined for three rabbits 120 minutes after treatment and showed significant signal heterogeneity at individual aortic levels. The high cholesterol rabbit administered targeted nanoparticles in particular manifests the greater overall enhancement, but "hot spots" are present in all three samples.

Histological determinations confirmed the colocalization of the $\alpha_v\beta_3$ integrin epitopes with the vascular endothelium. H&E staining showed that there was mild intimal thickening after 80 days in the cholesterol-fed rabbits only. Immunocytochemical analyses revealed prominent staining for $\alpha_v\beta_3$ at the adventitia-media interface in the cholesterol-fed rabbits and PECAM staining, indicative of vascular endothelium, colocalized with the $\alpha_v\beta_3$ integrin epitopes at the adventitia-media interface. This was observed much more prominently in the cholesterol-fed rabbits, confirming the presence of an expanded vasa vasorum associated with inflammatory markers.

A "region-growing" segmentation algorithm for semi-automated analysis of signal intensities within the aortic wall images for each imaged slice was developed. The aortic lumen was isolated in each two-dimensional image through the use of a seeded "region-growing" algorithm that iteratively increased the segmented area by evaluating the surrounding pixels for their similarity to the previously segmented pixels. Once a pre-determined threshold for similarity was reached, growth terminated. By increasing the width of this segmentation to include the wall and subtracting the previously segmented lumen, only a binary mask of the aortic wall and some additional background pixels remained. Further thresholding was used to remove the background pixels so that only the aortic wall was segmented. After segmentation, the mean intensity of the wall in each slice and time point was subtracted from the mean intensity in the same slice at baseline. The algorithm kernel was adapted from a procedure developed by Dr. Michael Brown at the Hong Kong University of Science and Technology available at a www address of cs.ust.hk/~brown/.

This procedure was applied uniformly to all aortic data sets and produces a circumferential region of interest for the entire aortic wall as illustrated in FIG. 7A. MRI signal intensity before and after nanoparticle injection was quantified within the entire segmented aortic region at each level, and in adjacent skeletal muscle regions of interest that were selected at random. Signal intensity was normalized to the signal from a fiduciary marker (a $Gd^{3+}$-DTPA/saline solution in a test tube phantom) that was placed within the field of view. The percent change in signal intensity after nanoparticle injection was calculated for images at 15, 60, and 120 minutes after injection. General linear modeling with Duncan's multiple-range testing of group differences (SAS, Inc., Cary, N.C.) was used to determine the significance of differences in MRI signals ($p<0.05$).

Figure 8:
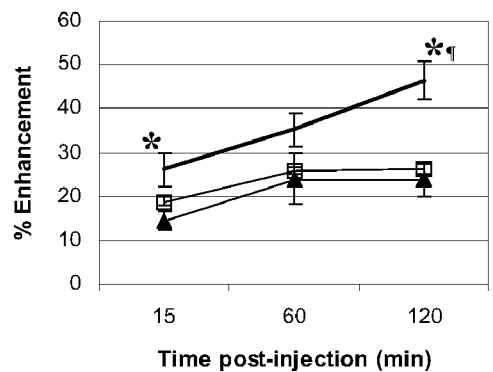
FIGS. 8A and 8B show the percent enhancement of MRI signal in aorta and muscle using targeted and non-targeted particles.
Figure 8:
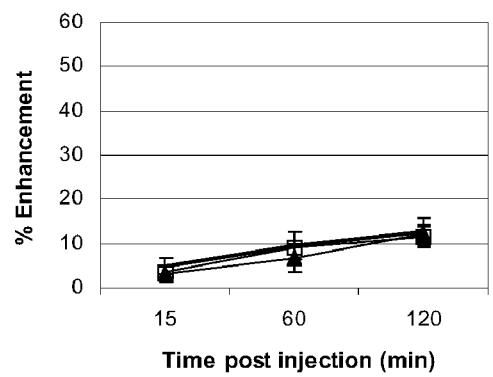

Quantification of the aortic signal enhancement was conducted conservatively by calculating the average aortic enhancement for a single rabbit across all aortic levels that had been imaged, and then averaging these single rabbit values for an entire experimental group. FIG. 8A shows that immediately after injection of targeted nanoparticles (within approximately 15 minutes), the signal in the entire aortic wall was enhanced by 26±3.8% for all rabbits. By 120 minutes, the signal from the entire aortic wall was enhanced further by 47±15.4% over baseline. The entire aortic wall of all cholesterol-fed rabbits that received non-targeted nanoparticles also enhanced by 19±10.8% within 15 minutes, but remained stable from 60-120 minutes (26±1%), which represents only about half of the signal augmentation as for the specifically targeted enhancement.

In the control-diet rabbits, significant aortic wall enhancement was observed immediately after injection of targeted nanoparticles to a level equivalent to that of the cholesterol-fed rabbits at that time point (14.5±12.2%). However, after 2 hours, the signal was little increased (23.7±3.7%). Thus, the signal enhancement in the entire aortic wall for cholesterol-fed animals approximately doubled that for control-diet animals by 120 minutes.

The signal enhancement observed in the adjacent skeletal muscle (FIG. 8B) for any group at any time period was far less than that for any of the aorta groups, and just bordered statistical significance ($p<0.051$). This trend was not related statistically to nanoparticle type or to feeding regimen by ANOVA.

The data indicate that specific identification of $\alpha_v\beta_3$ epitopes in vascular inflammation is possible with high resolution MRI in vivo.

Previous pharmacokinetic analyses indicate that particle clearance is biexponential with a $\beta$-elimination rate of 1-1.5 hours. These properties are not affected by addition of the ligand or the gadolinium chelate. Accordingly, the concentration gradient driving nonspecific accumulation of molecularly-targeted nanoparticles in aorta or muscle should be diminishing by 120 minutes (which is consistent with the present data showing a plateau for nonspecific signal enhancement in aorta: see FIG. 8). On the contrary, the process of specific binding to $\alpha_v\beta_3$ epitopes should increase for a number of half lives since the nanosystem is expected to exist in large ligand excess in the circulation as compared with the low prevalence of molecular epitopes on the neovasculature, given that approximately 100 trillion nanoparticles were injected in an average i.v. dose. The greater nonspecific enhancement in aortic wall versus that for muscle likely relates to the expansion of the sinusoid-like vasa vasorum that provides both a larger distribution volume, and simultaneously a greater local concentration of paramagnetic nanoparticles that are less subject to signal nulling by our particular "black blood" imaging method. Because inflow/outflow in the vasa vasorum is likely to be much slower than that in the aortic lumen, signal nulling should be more effective for the aortic lumen blood pool than for that of the vasa vasorum.

Targeted paramagnetic nanoparticles can thus be used with MRI in small i.v. doses with routine clinical imaging approaches to delineate vascular inflammation and/or angiogenesis in early stage atherosclerosis.

EXAMPLE 3

Restenosis Model

Domestic pigs, healthy, diabetic, or hyperlipidemic, are sedated with telazol cocktail (1 ml/23 kg IM) followed by intubation and 1-2% isoflurane anesthesia in oxygen. The ECG, blood gases and arterial blood pressure are monitored. Lidocaine, diltiazem, and/or nitroglycerin are used to treat vasospasm.

Following peripheral arterial access and sheath placement, an appropriate sized angioplasty balloon, e.g., 8 mm×2 cm balloon catheter; Proflex, Mallinckrodt Inc., St. Louis), is positioned at a cervical vertebral level (C-3 to C-5) and inflated multiple times (usually 3 times) to a pressure of 6 atmospheres for 30 seconds with 60 second pauses between inflations. A balloon-to-artery ratio of approximately 1.5 is typically employed. This procedure produces a consistent rupture of the internal elastic lamina and injury to the media.

Following the above carotid overstretch balloon-injury, an emulsion comprising nanoparticles, as described in Example 1, is administered via a local delivery catheter system. The delivery system is a paired balloon catheter or an mechanical perfusion delivery/vacuum extraction system. Targeted- or control nanoparticles, or saline alone are delivered locally and allowed to incubate for between 1 and 15 minutes. An MR angiogram is performed prior to carotid vascular wall imaging studies.

MRI scanning is performed on a 1.5 Tesla clinical scanner (NT Intera CV, Philips Medical Systems, Best, Netherlands) or comparable clinical system at 1.0T to 7.0T. Appropriate coils include a quadrature head/neck birdcage coil, circular surface coils, phased-array (Synergy) coils. For research analyses, gadolinium diethylenetriaminepentaacetic acid (Gd-DTPA) doped water standards are placed within the high-resolution field of view (FOV) to serve as an image signal intensity standard; this is not required for clinical application. MR image analysis is performed off-line with an EasyVision v5.1 workstation (Philips Medical Systems, Best, Netherlands) or similar image manipulation system.

Figure 9:
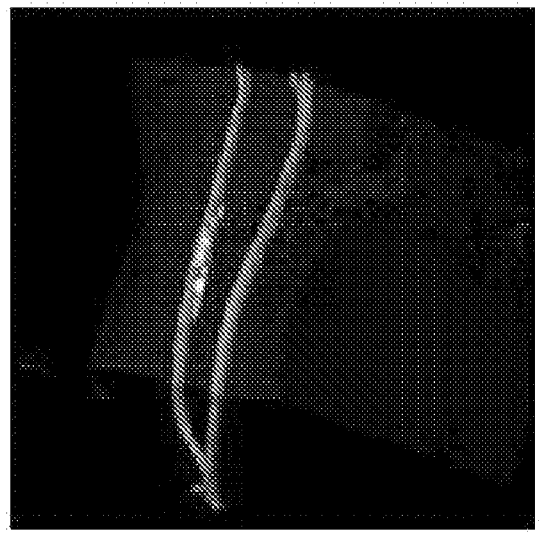
FIG. 9 shows a 3-D angiogram of carotid arteries of domestic pigs following angioplasty with $\alpha_v\beta_3$-targeted paramagnetic nanoparticles illustrating balloon overstretch injury pattern.

FIG. 9 shows a 3-dimensional reconstruction of the contrast-enhanced balloon injury pattern using $\alpha_v\beta_3$-targeted paramagnetic nanoparticles. This reveals the spatial distribution of microfractures induced within the tunica media. These data, impossible to detect with routine X-ray angiography, can provide quantitative assessments of wall injury that have prognostic importance to subsequent revascularization complications, including restenosis.

In addition to comprising the $\alpha_v\beta_3$ targeting moiety, the nanoparticles are supplied with antiproliferative agents such as radionuclides, paclitaxel or rapamycin.

What is claimed is:

1. A method to deliver an emulsion comprising nanoparticles to a target tissue, wherein said target tissue is characterized by high levels of $\alpha_v\beta_3$ integrin, which method comprises administering to a subject comprising such tissue an emulsion of nanoparticles wherein said nanoparticles are coupled to a ligand specific for $\alpha_v\beta_3$ integrin, wherein said nanoparticles consist of liquid perfluorocarbon cores coated with lipid/surfactant, and wherein the coupling of said nanoparticles to the ligand is through a covalent linkage, through a spacer, to a component of the lipid/surfactant coating, and wherein the ligand comprises a residue of the formula

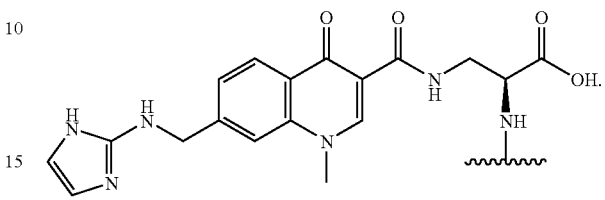

2. The method of claim 1, wherein said nanoparticles further include at least one magnetic resonance imaging (MRI) contrast agent.

3. The method of claim 2, wherein said MRI contrast agent is a chelated paramagnetic ion.

4. The method of claim 3, wherein said chelating agent comprises diethylenetriaminepentaacetic acid (DPTA) or 1,4,7,10-tetraazacyclododecane-1,4,7,10-tetraacetic acid (DOTA) and the paramagnetic ion is gadolinium ion.

5. The method of claim 1, wherein said nanoparticles further include at least one biologically active agent.

6. The method of claim 5, wherein said biologically active agent is a hormone or pharmaceutical compound.

7. The method of claim 2, which further includes allowing the $\alpha_v\beta_3$-specific ligand to bind to the target tissue; and obtaining a magnetic resonance image of said target tissue.

8. The method of claim 1 wherein said residue is coupled through a spacer to a component of the lipid/surfactant coating that is a phosphatidyl lipid.

9. The method of claim 8 wherein the ligand coupled to the component of the lipidisurfactant coating is of the formula

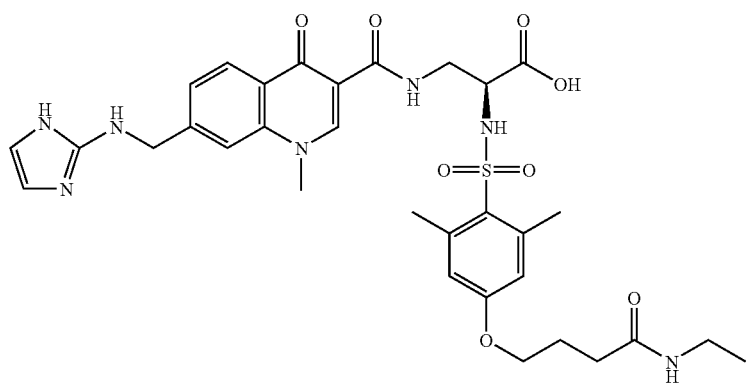

-continued
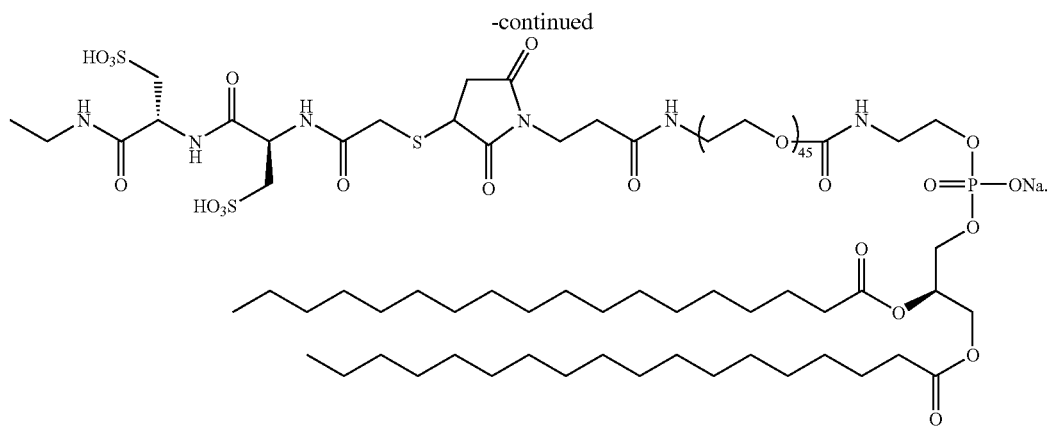
* * * * *